United States Patent [19]

Kobayashi et al.

[11] 4,390,618
[45] Jun. 28, 1983

[54] SILVER HALIDE PHOTOGRAPHIC LIGHT-SENSITIVE MATERIALS

[75] Inventors: Hidetoshi Kobayashi; Toshirou Takahashi; Shigeo Hirano; Takeshi Hirosa; Keiichi Adachi, all of Minami-ashigara, Japan

[73] Assignee: Fuji Photo Film Co., Ltd., Kanagawa, Japan

[21] Appl. No.: 357,930

[22] Filed: Mar. 15, 1982

[30] Foreign Application Priority Data

Mar. 13, 1981 [JP] Japan ................................. 56-36051

[51] Int. Cl.³ ............................................. G03C 1/40
[52] U.S. Cl. ................................. 430/543; 430/553; 430/555; 430/557; 430/558; 430/955
[58] Field of Search ............... 430/553, 555, 557, 469, 430/487, 558, 955, 543

[56] References Cited

U.S. PATENT DOCUMENTS 3,253,924  5/1966  Loria et al. ......................... 430/553
4,168,977  9/1979  Takada et al. ....................... 430/446
4,224,401  9/1980  Takada et al. ....................... 430/437
4,248,962  2/1981  Lau ..................................... 430/553

Primary Examiner—J. Travis Brown
Attorney, Agent, or Firm—Sughrue, Mion, Zinn, Macpeak & Seas

[57] ABSTRACT

A silver halide photographic light-sensitive material is described comprising a layer containing a coupler compound represented by formula (I)

A—B     (I)

wherein A represents a residue of a compound capable of undergoing a coupling reaction with an oxidation product of an aromatic primary amine developing agent, by the removal of one hydrogen atom from the active position of said compound, and B represents a group which is released by the coupling reaction and exhibits a development accelerating function.

4 Claims, No Drawings

SILVER HALIDE PHOTOGRAPHIC LIGHT-SENSITIVE MATERIALS

FIELD OF THE INVENTION

The present invention relates to novel photographic color couplers or colorless couplers, color photographic light-sensitive materials containing these couplers and an image forming process using these couplers.

BACKGROUND OF THE INVENTION

It has been well known that after a silver halide photographic light-sensitive material is exposed to light, an oxidized aromatic primary amine developing agent reacts with dye forming couplers to form color images. In this process, color reproduction by a conventional subtractive process is used to form color images composed of cyan, magenta, and yellow dyes, which are the complementary colors of red, green, and blue, respectively. The reaction of the couplers with the oxidation product of the color developing agent is carried out at an active site (usually referred to as the coupling position). The coupler having a hydrogen atom as a substituent at this active site is a 4-equivalent coupler, i.e., a coupler which stoichiometrically requires 4 moles of silver halide having a development nucleus as an oxidizing agent for forming 1 mol of dye.

On the other hand, a coupler having a group releasable in a state of an anion (which herein refers to "coupling-off group") as a substituent at the active site is a 2-equivalent coupler, i.e., a coupler which requires only 2 mols of silver halide having a development nucleus for forming 1 mol of dye. Accordingly, the processing time for the light-sensitive materials can be shortened, and the sharpness of the formed color images is improved when the 2-equivalent coupler is used, as compared with using the 4-equivalent coupler, because it is possible to reduce the amount of silver halide in the light-sensitive layer and to thin the thickness of the layer. In 2-equivalent couplers, it is possible to change the coupling activity to the color developing agent by changing the property of coupling-off group.

Furthermore, a 2-equivalent coupler which has the effect of restraining development by means of the released coupling-off product is called development inhibitor releasing coupler (DIR coupler), which restrains the development in proportion to an amount of development silver formed. Accordingly, it shows effects such as fine granulation of image, control of gradation, improvement of color reproduction, etc. Further, it can be utilized for a diffusion transfer process by utilizing its function to adjacent layers.

Also, when a diffusible dye portion is substituted as the coupling-off group at the active site of the 2-equivalent coupler, it is possible to use the coupler in a diffusion transfer process for forming diffusible dye images on an image receiving layer by utilizing a dye released. This kind of coupler is usually referred to as a diffusible dye releasing (DDR) coupler.

Additionally, certain kinds of colored 2-equivalent couplers shows a masking effect for color correction of dye images. These kinds of coupler are referred to as colored 2-equivalent coupler.

As described above, it is possible to provide various functions in 2-equivalent couplers by changing the coupling-off group.

Silver halide has been widely used in the photographic field, because it has the highest sensitivity of known light-sensitive materials. However, all of silver halides are not used sufficiently as light-sensitive elements, and it causes lowering of sensitivity of the silver halide photographic light-sensitive materials, deterioration of granularity deterioration of sharpness, etc. This is believed to be ascribable to the uneven development rate of each emulsion grain one another and in consequence existence of emulsion grains of retarded development, because of various causes such as differences of sensitive properties and development properties of silver halide emulsions, flickering of light at exposure or uneven development, etc.

In order to accelerate the development of emulsion grains exhibiting retarded development, it has been proposed hitherto to add various kinds of development accelerators such as hydrazine compounds, amine compounds, 1-phenylpyrazoline-3-one derivatives, hydroquinone derivatives, hydrogen peroxides, etc., to an emulsion layer or a developing solution, particularly, for black-and-white light-sensitive materials. However, they are not practically used because they frequently cause increases of fog or deterioration of granularity.

The present invention relates to couplers which release a diffusible development accelerator as the coupling-off group. These are referred to as development accelerator releasing (DAR) couplers. The conception of such development accelerator releasing (DAR) couplers have been disclosed in U.S. Pat. Nos. 3,214,337 and 3,253,924 and Japanese Patent Application (OPI) No. 17437/76 std. OPI def. (the term "OPI" as used herein refers to a "published unexamined Japanese patent application"). All of these disclosed couplers release a thiocyanic acid ion to accelerate the development by means of a dissolution physical development function. However, because many conventionally used emulsions are surface development type emulsions, the granularity resulting is inferior, because the increased rate of the number of development initiation points by the dissolution physical development is small and rather the development is accelerated by enlarging development initiation points.

SUMMARY OF THE INVENTION

An object of the present invention is to provide light-sensitive materials having high sensitivity which form images having good granularity.

Another object of the present invention is to provide light-sensitive materials having high color densities and to light-sensitive materials containing an economical amounts of silver.

It has now been found that the objects of the present invention can be attained by imagewise acceleration of the development of the silver halide grains by using particular development accelerator releasing couplers.

Contrary to the previously proposed DAR couplers, the couplers of the present invention accelerate the development by significantly increasing the number of development initiation points by utilizing an electron donating reaction of the released reductive development accelerator into silver halide. Thus, the mechanism function thereof is different from that of the above described dissolution physical development couplers, and the development accelerating function is very large. Particularly, the granularity does not deteriorate because the development is accelerated by increasing the number of development initiation points.

The objects of the present invention have been attained by silver halide photographic light-sensitive materials comprising a layer containing a coupler compound represented by formula (I)

A—B                          (I)

wherein A represents a residue of a compound capable of undergoing a coupling reaction with an oxidation product of an aromatic primary amine developing agent by the removal of one hydrogen atom from the active position of said compound, and B represents a group which is released by the coupling reaction and exhibits a development accelerating function.

DETAILED DESCRIPTION OF THE INVENTION

Examples of the group which exhibits the development accelerating function include compounds derived from thiourea, hydrazine, rhodanine, thioamide, etc. Hydrazine compounds are particularly effective.

Among compounds represented by formula (I), compounds represented by formula (II) are particularly preferred.

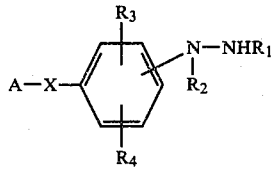

A in formula (II) represents a residue of a compound capable of undergoing a coupling reaction with an oxidation product of an aromatic primary amine developing agent by the removal of one hydrogen atom from the active position of said compound. More particularly, A can be a cyan coupler residue, a magenta coupler residue, a yellow coupler residue, or a non-coloring coupler residue. X represents a divalent linking group.

$R_1$ in formula (II) represents a formyl group, an acyl group (an acetyl group, a propionyl group, a trifluoroacetyl group, a benzoyl group, etc.), a sulfonyl group (a methanesulfonyl group, a benzenesulfonyl group, etc.), an alkoxycarbonyl group (an ethoxycarbonyl group, etc.), a carbamoyl group (a dimethylaminocarbonyl group, etc.) or a sulfamoyl group (a dimethylaminosulfonyl group, etc.). $R_2$ represents a hydrogen atom, an acetyl group, an ethoxycarbonyl group, or a methanesulfonyl group. Each of $R_3$ and $R_4$ represents a hydrogen atom, a lower alkyl group (a methyl group, etc.), a lower alkoxy group (a methoxy group, etc.) or a halogen atom (fluorine, chlorine, bromine, or iodine).

In formula (II), X represents a divalent group linking A and B which contains a hetero atom therein and X is bonded to A through said hetero atom. X comprises one or more divalent groups selected from alkylene, phenylene, alkenylene, ether, thioether, amide, thioamide, sulfonamide, ester, sulfon, urea, thiourea, and a heterocyclic ring.

Examples of the cyan coupler residues represented by A include phenol couplers and naphthol couplers. Examples of the magenta coupler residues include 5-pyrazolone couplers, pyrazolobenzimidazole couplers, cyanoacetylcoumarone couplers, ring-opened acyl acetonitrile couplers, and inidazolone couplers. Examples of the yellow coupler residues include acylacetamide couplers (benzoylacetanilide coupler and pivaloylacetanilide coupler, etc.), dibenzoylmethane couplers and malondianilide couplers, etc. Examples of the colorless coupler residues include ring-opened or cyclic active methylene compounds (for example, indanone, cyclopentanone, malonic acid diester, imidazolinone, oxazolinone and thiazolinone, etc.). Preferred coupler residues represented by A used according to the present invention can be represented by the formulae (III), (IV), (V), (VI), (VII), (VIII), (IX), (X), and (XI), viz.,

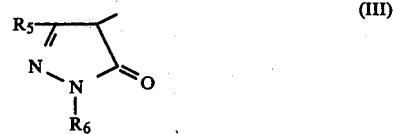

wherein $R_5$ represents an acylamino group, an anilino group or a ureido group, and $R_6$ represents a phenyl group which may be substituted with one or more halogen atoms, alkyl groups, alkoxy groups, or cyano groups;

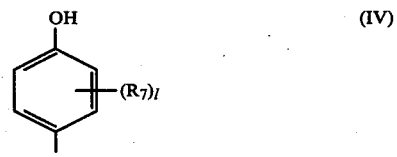

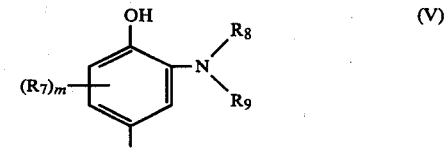

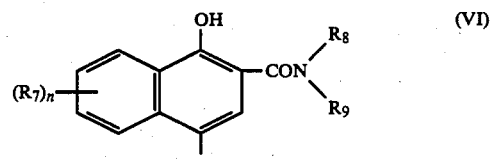

wherein $R_7$ represents a halogen atom, an acylamino group, or an aliphatic group, and each of $R_8$ and $R_9$ represents an aliphatic group, an aromatic group or a heterocyclic group, and one of $R_8$ and $R_9$ may represents a hydrogen atom, l represents an integer of 1 to 4, m represents an integer of 0 to 3, and n represents an integer of 0 to 4;

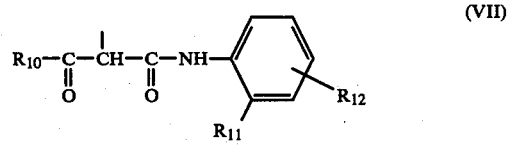

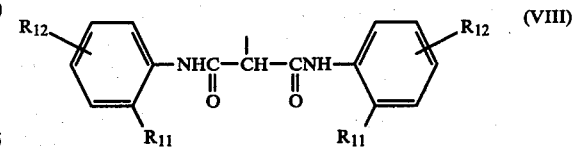

wherein $R_{10}$ represents a tertiary alkyl group or an aromatic group, $R_{11}$ represents a hydrogen atom, a halogen atom, or an alkoxy group, and $R_{12}$ represents an acylamino group, an aliphatic group, an alkoxycarbonyl group, a sulfamoyl group, a carbamoyl group, an alkoxy group, a halogen atom, or a sulfonamido group;

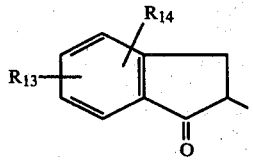 (IX)

wherein $R_{13}$ represents an aliphatic group, an alkoxy group, a mercapto group, an acylamino group, an alkoxycarbonyl group, a sulfonamido group, a carbamoyl group, a sulfamoyl group, an alkoxysulfonyl group, an aryloxysulfonyl group, an acyl group, a diacylamino group, an alkylsulfonyl group or an arylsulfonyl group, and $R_{14}$ represents a halogen atom, an alkoxy group, an acyl group, a nitro group, an alkylsulfonyl group or an arylsulfonyl group;

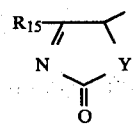 (X)

wherein $R_{15}$ represents an aliphatic group or an aromatic group, and Y represents an oxygen atom, a sulfur atom, or imino group; and

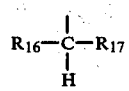 (XI)

wherein each of $R_{16}$ and $R_{17}$ represents

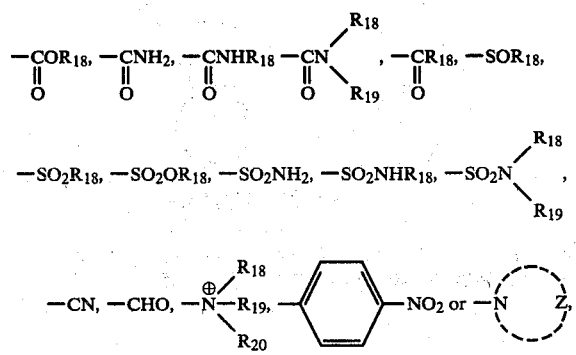

wherein each of $R_{18}$, $R_{19}$ and $R_{20}$ represents an aliphatic group, an aromatic group, or a heterocyclic ring, and Z represents a non-metallic atomic group necessary to form a 5- or 6-member ring together with the nitrogen atom, and $R_{16}$ and $R_{17}$ together may form a 5- or 6-membered non-metallic ring.

X in formula (II) represents a divalent group composed of one or more selected from

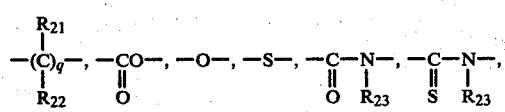

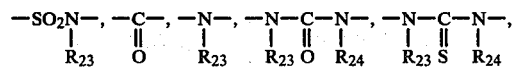

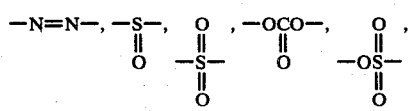

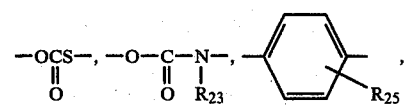

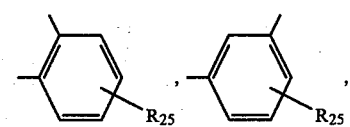

and divalent heterocyclic groups (for example, divalent groups of pyrrole, pyrazole, imidazole, triazole, benzimidazole, benzotriazole, thiadiazole, benzothiazole, oxazole, benzoxazole, oxadiazole, hydantoin, 2,4-oxazolidinedione, urazol, succinimide and phtalimide) (which may form a ring), which links to A through a nitrogen, oxygen, or sulfur atom.

In the foregoing formulae, each of $R_{21}$ and $R_{22}$ represents a hydrogen atom, a halogen atom, an alkyl group, or an alkoxy group, $R_{23}$ and $R_{24}$ each represents a hydrogen atom, an acyl group, or a sulfonyl group, $R_{25}$ represents a hydrogen atom, an alkyl group, an alkoxy group, an acyl group, a sulfonyl group, a halogen atom, or a nitro group, and q represents an integer of 1 to 10 (wherein each of $R_{21}$ and $R_{22}$ may be the same or different when q is 2 or more).

Examples of the divalent linking group represented by X are described below, wherein

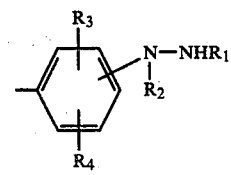

in formula (II) is represented by D.

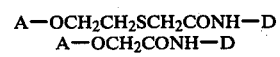

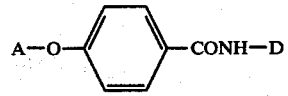

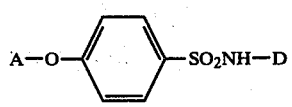

-continued
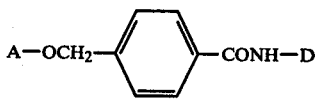
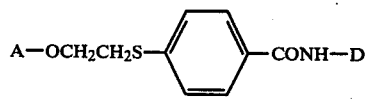
A—OCH₂CH₂SO₂CH₂CONH—D
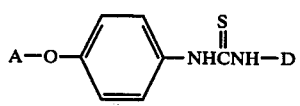
A—OCH₂CH₂O—D
A—OCH₂CH₂SO₂NH—D
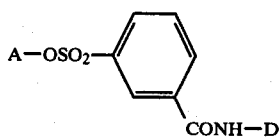
A—OCH₂CH₂SCHCONH—D
          |
          CH₂COOH
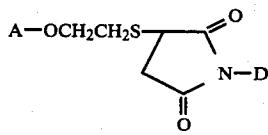
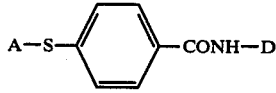
A—SCH₂CH₂CONH—D
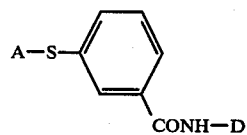
-continued
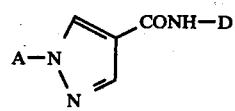
A—SCH₂CH₂O—D
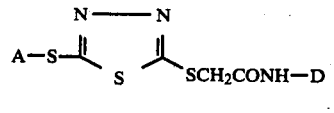
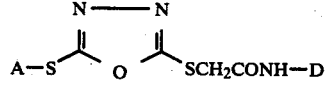
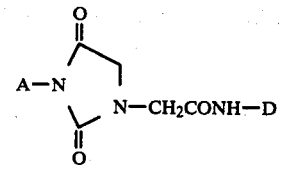
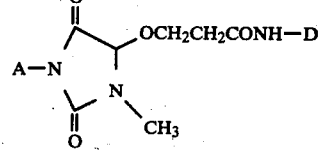
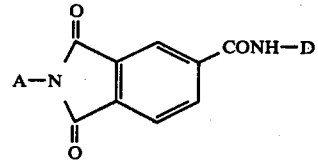
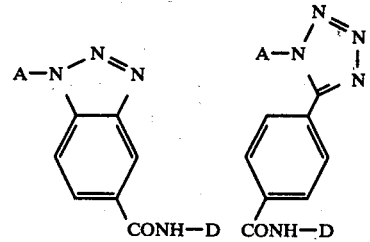
Examples of the coupler compound used according to the present invention are set forth below.
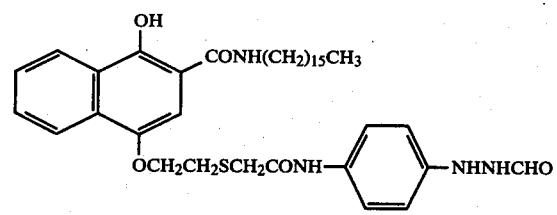
(1)

-continued
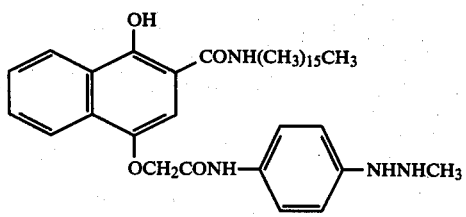
(2)
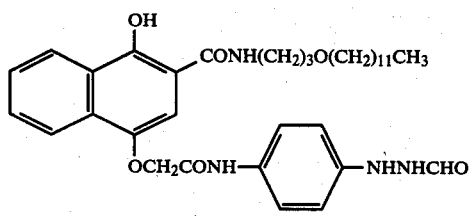
(3)
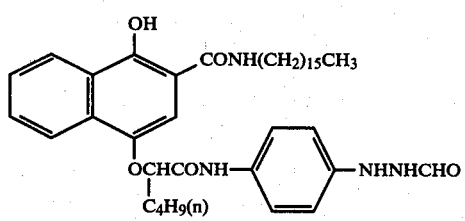
(4)
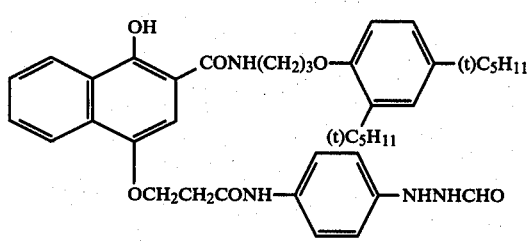
(5)
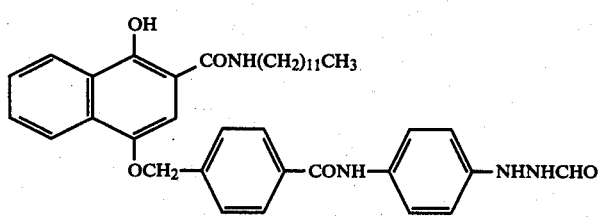
(6)
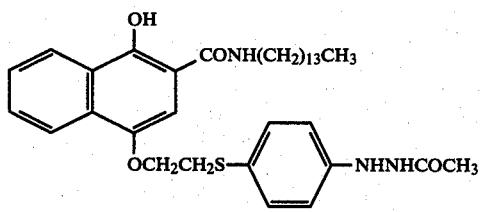
(7)
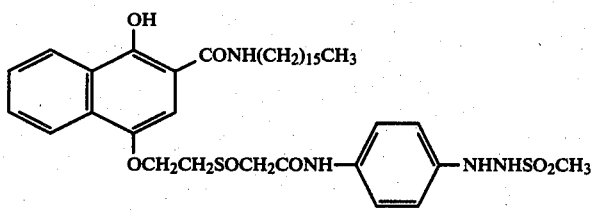
(8)

-continued
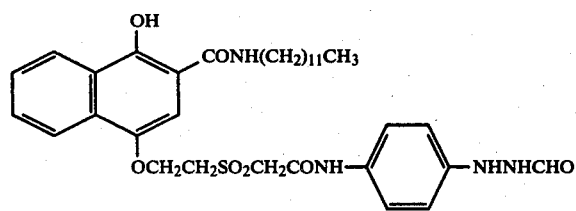
(9)
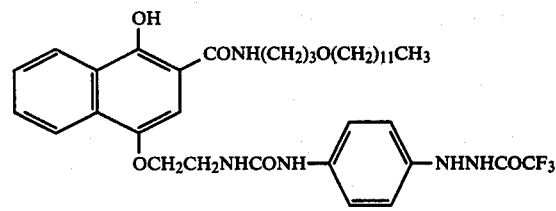
(10)
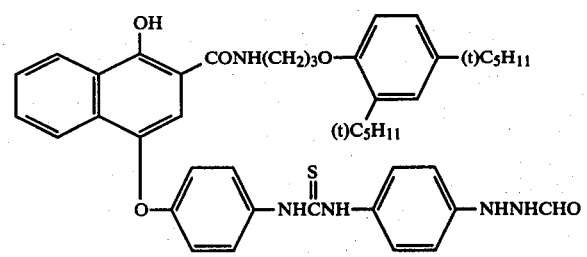
(11)
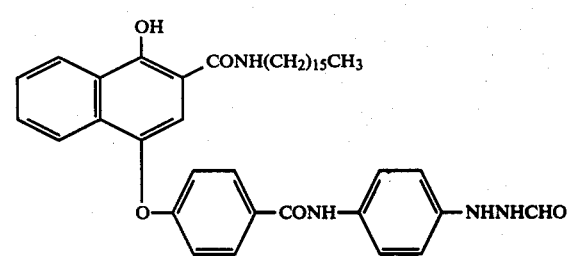
(12)
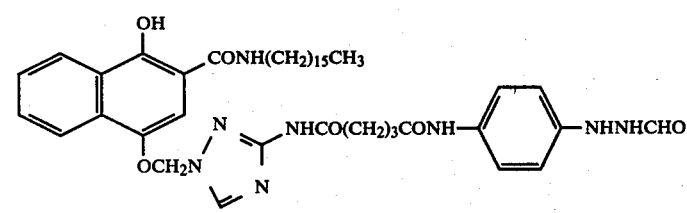
(13)
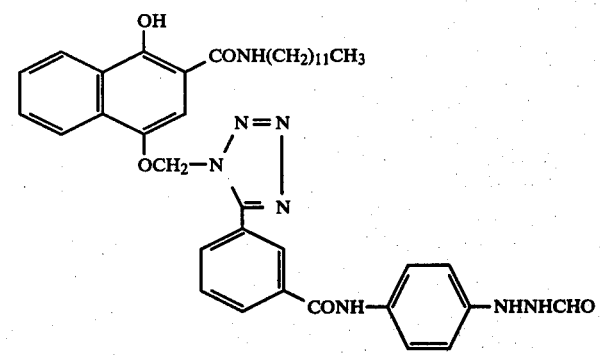
(14)

-continued
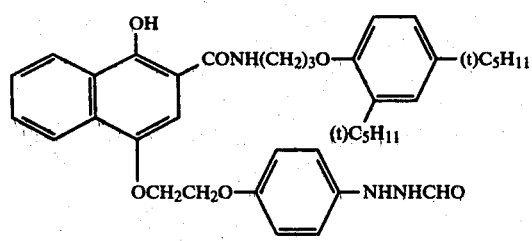
(15)
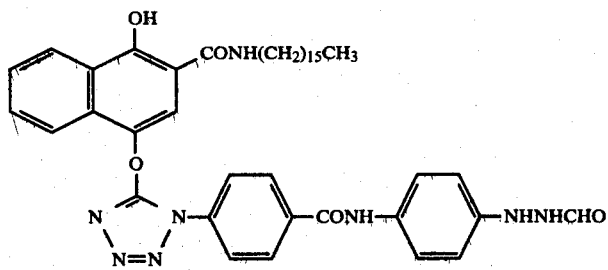
(16)
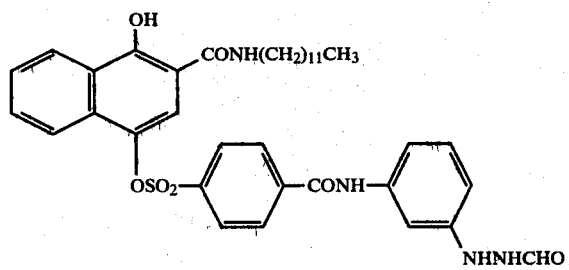
(17)
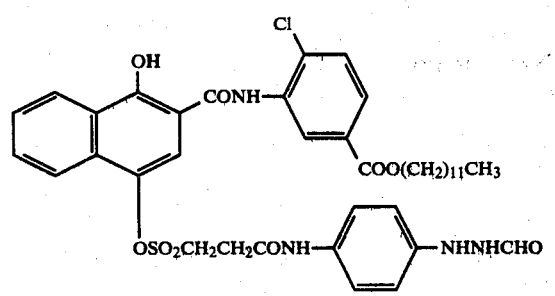
(18)
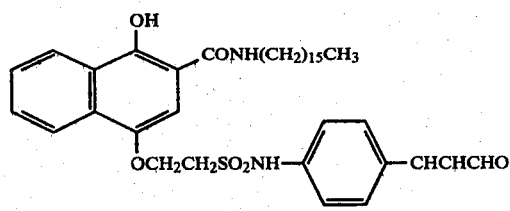
(19)
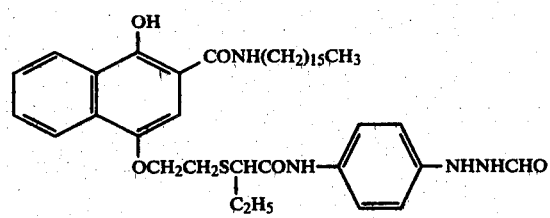
(20)

-continued
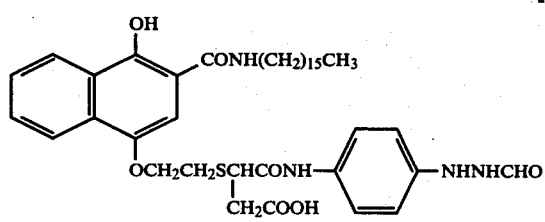
(21)
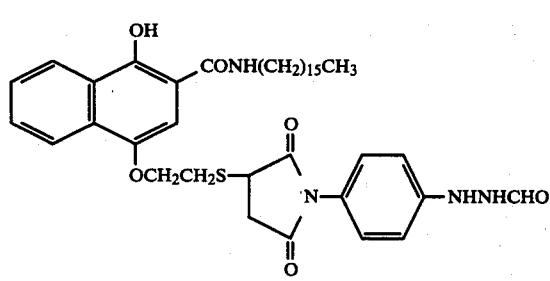
(22)
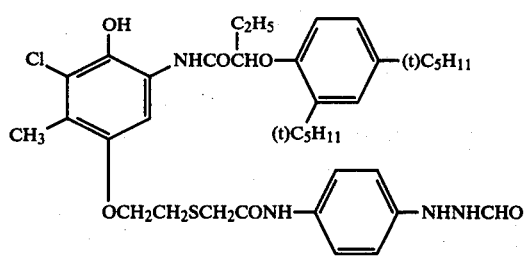
(23)
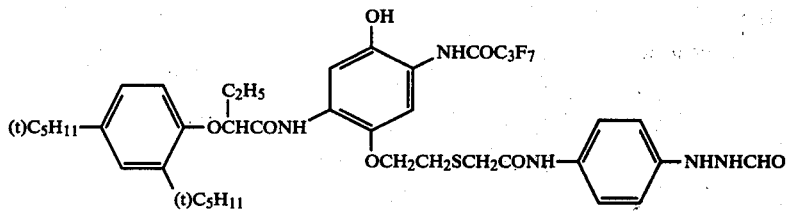
(24)
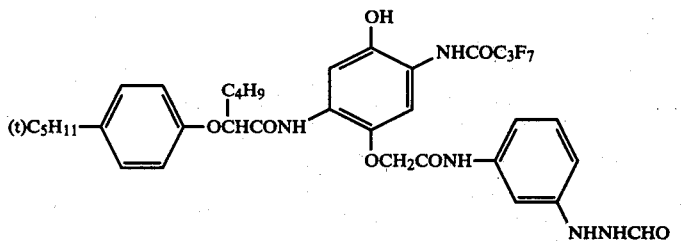
(25)
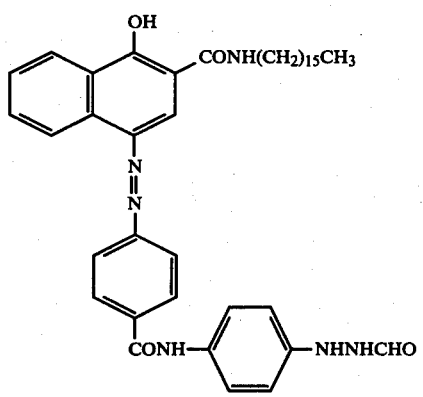
(26)

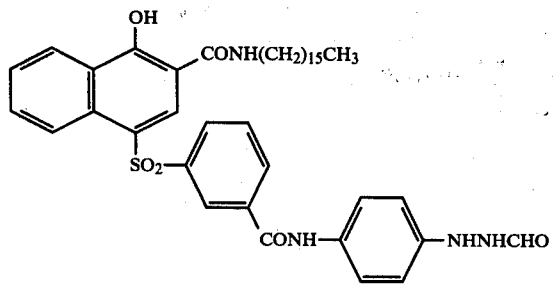
(27)
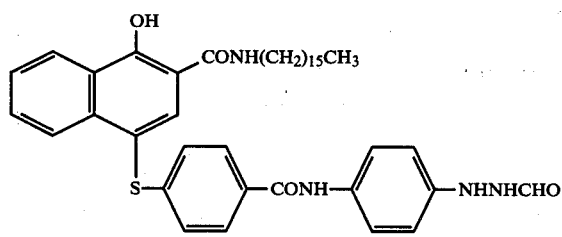
(28)
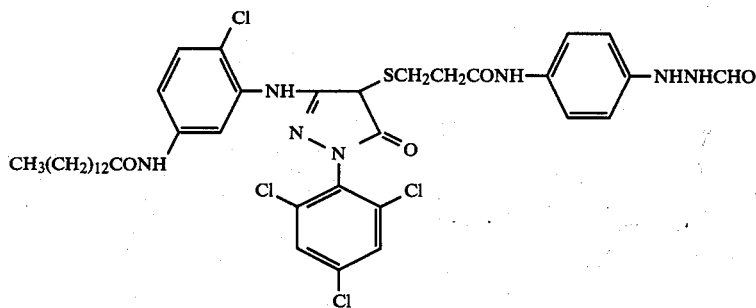
(29)
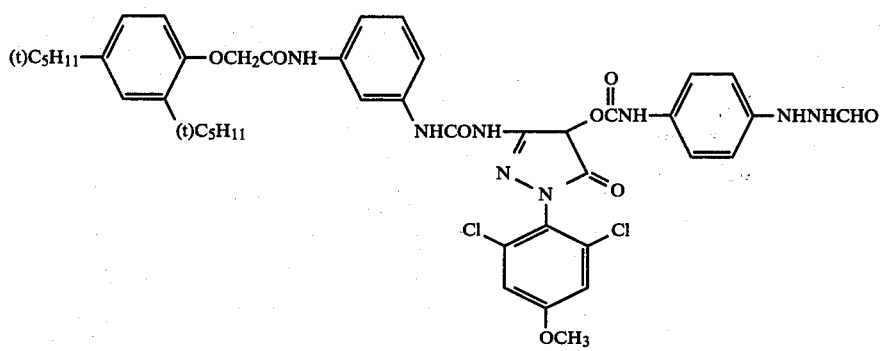
(30)
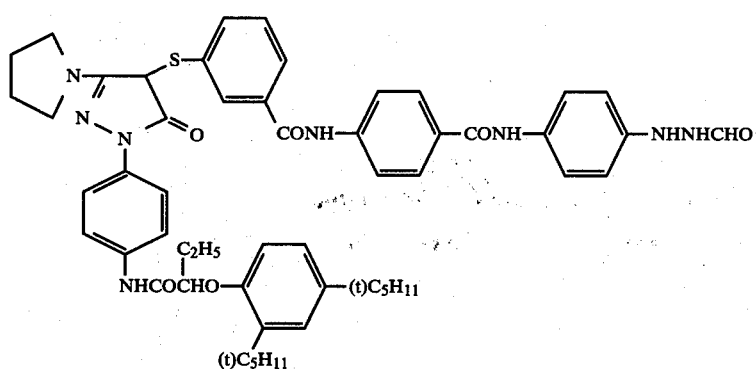
(31)

-continued
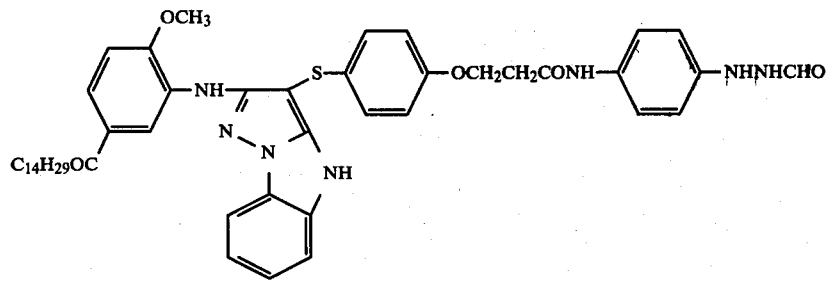
(32)
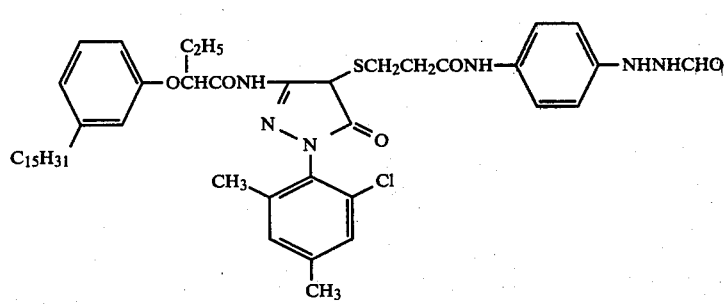
(33)
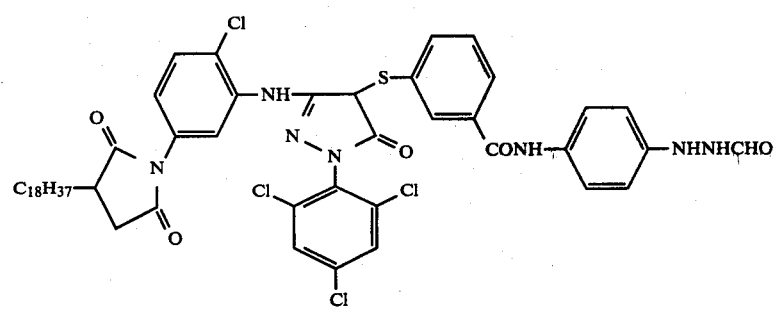
(34)
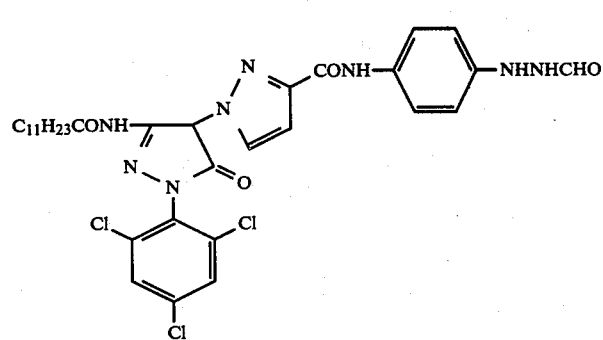
(35)
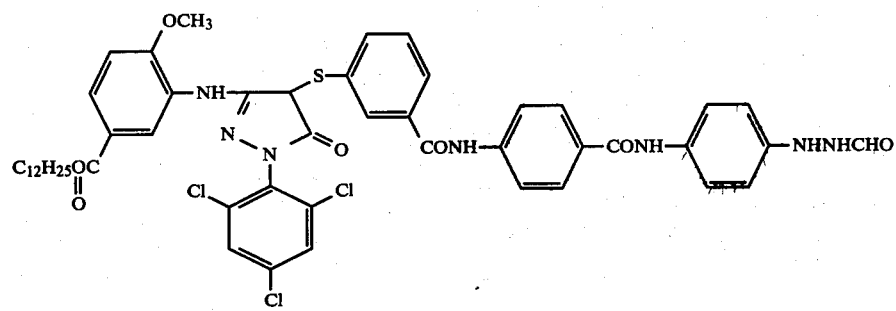
(36)

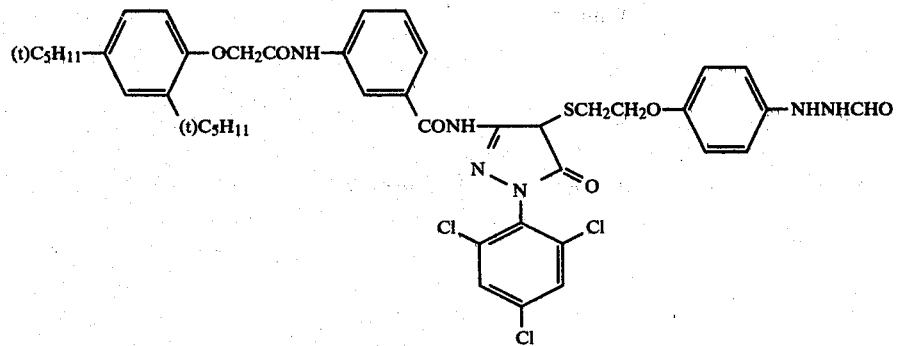
(37)
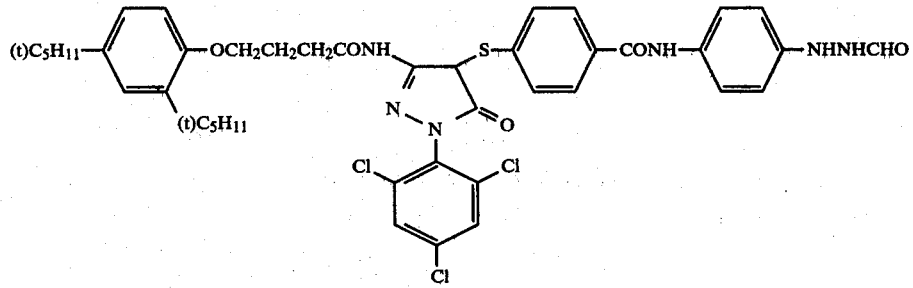
(38)
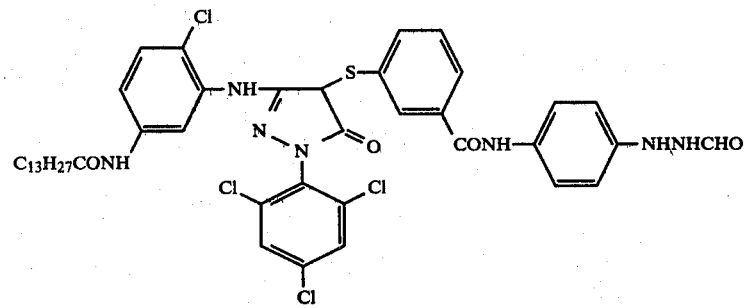
(39)
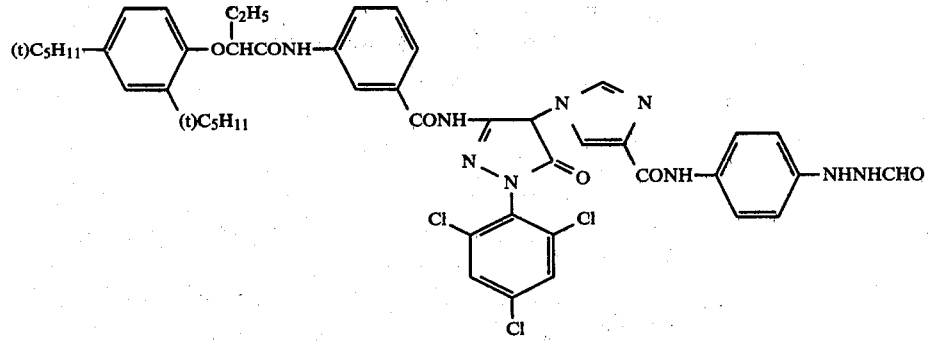
(40)
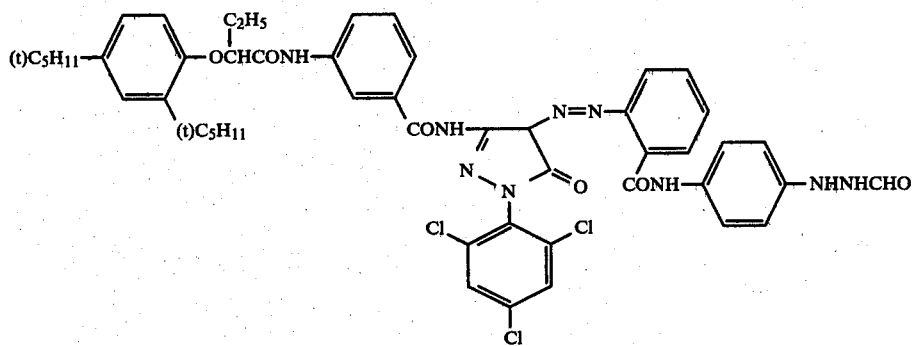
(41)

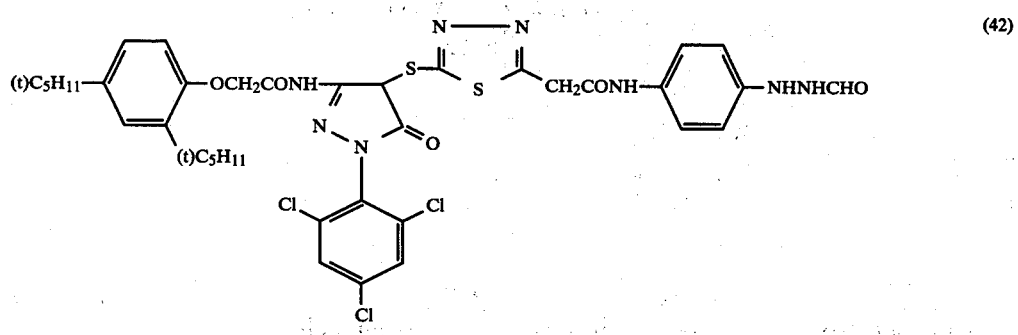
(42)
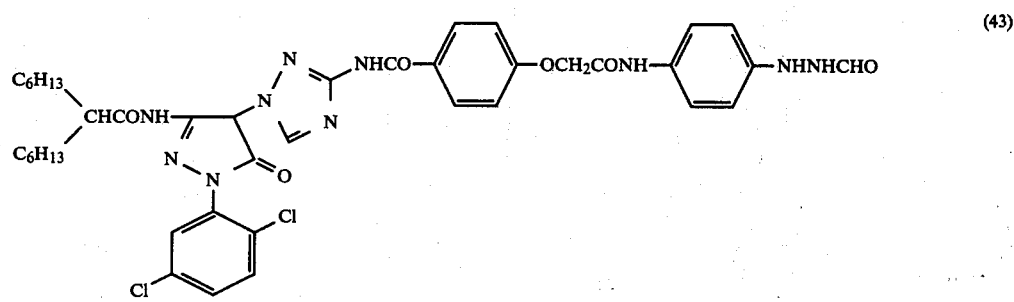
(43)
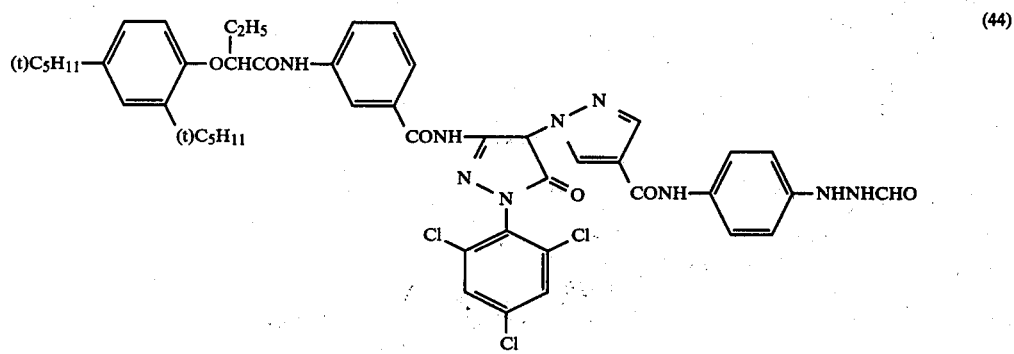
(44)
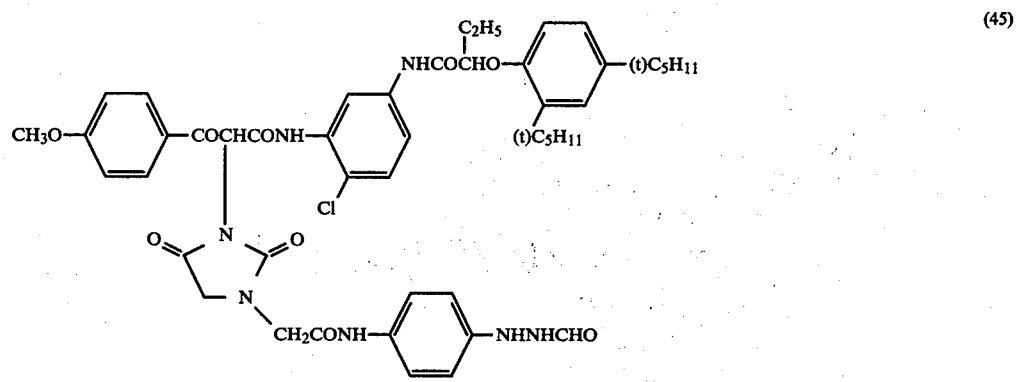
(45)

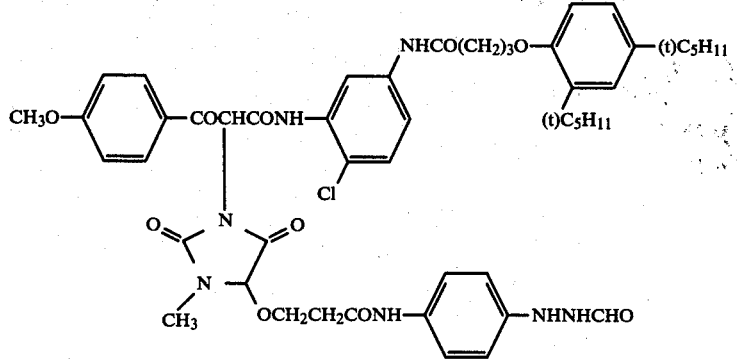
(46)
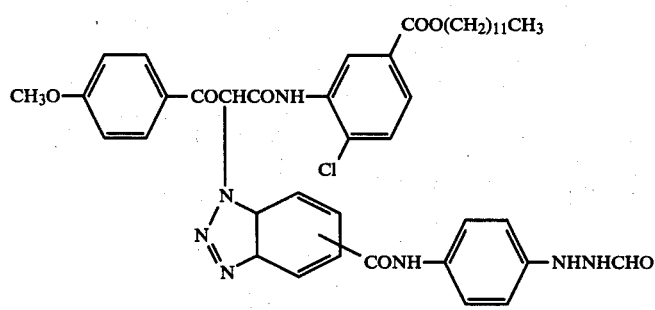
(47)
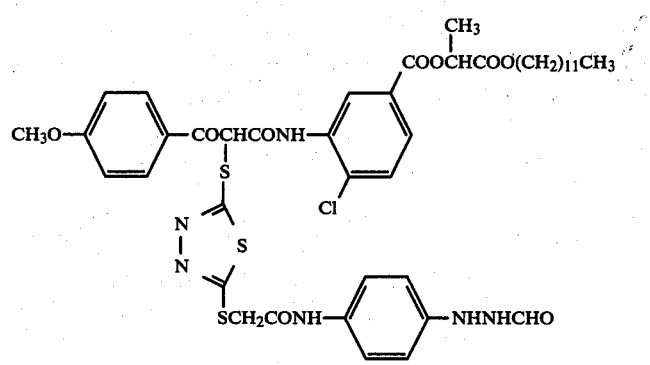
(48)
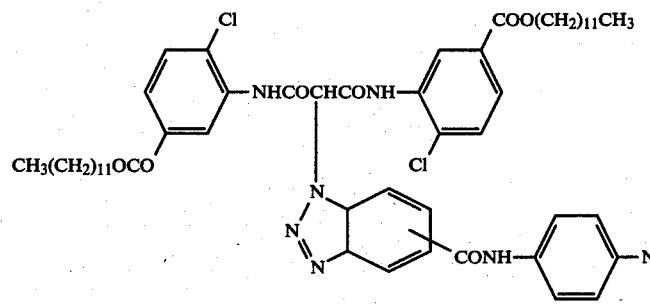
(49)
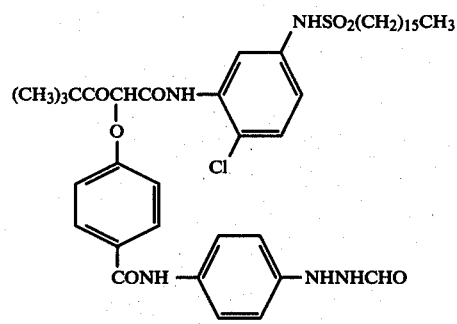
(50)

(51)
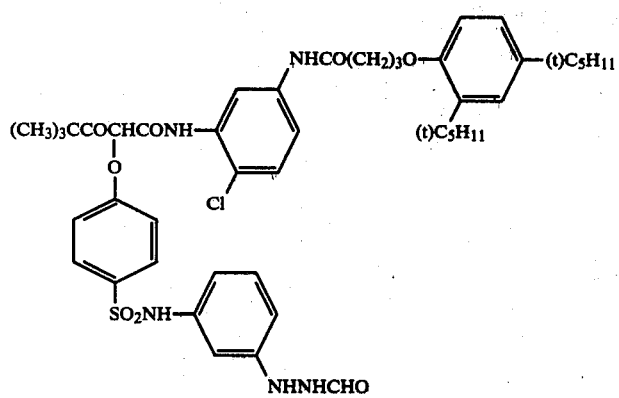
(52)
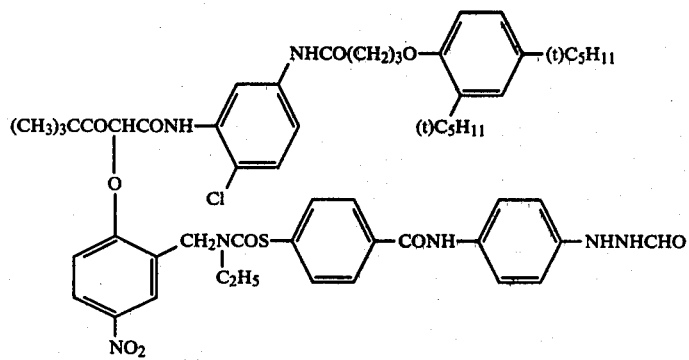
(53)
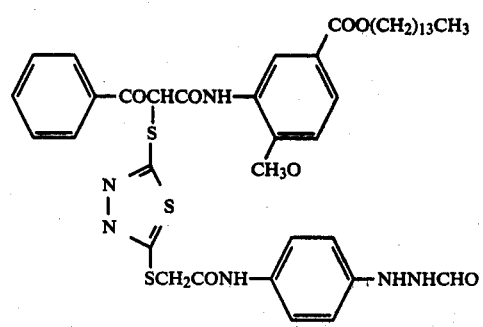
(54)
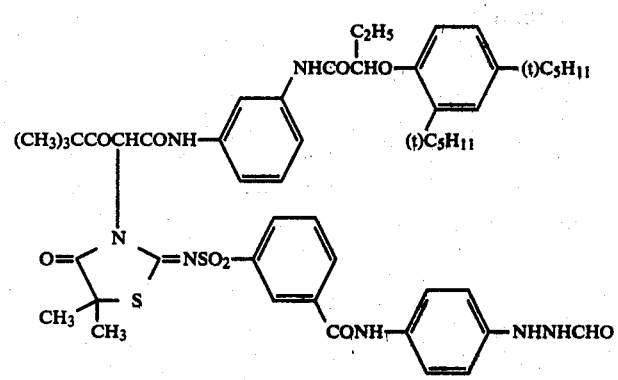

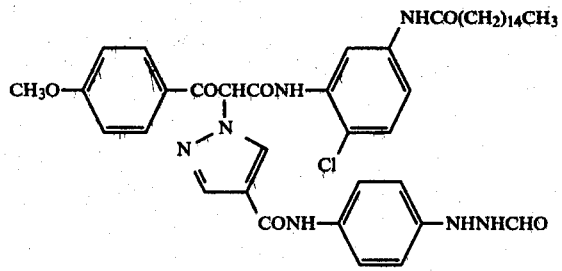
(55)
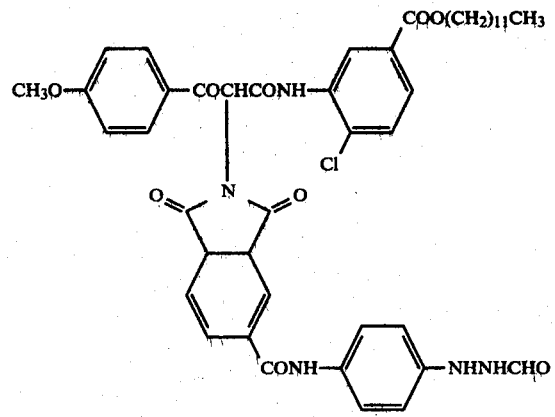
(56)
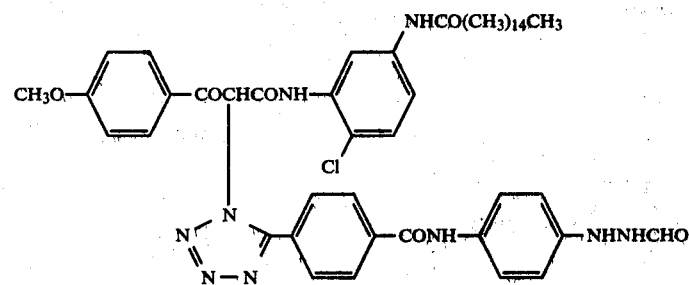
(57)
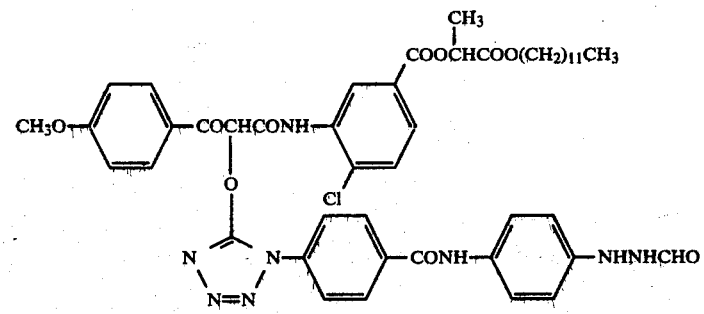
(58)
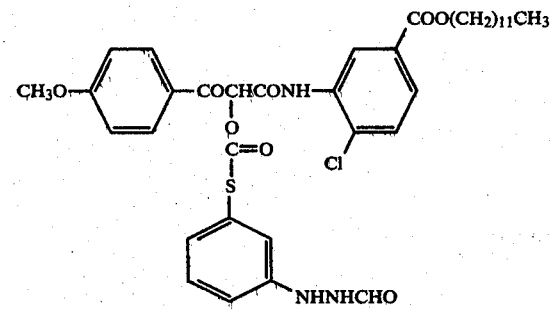
(59)

-continued
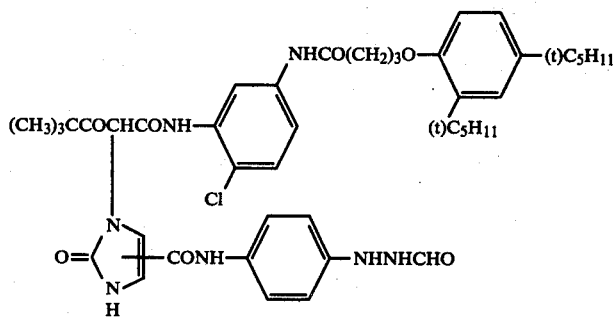
(60)
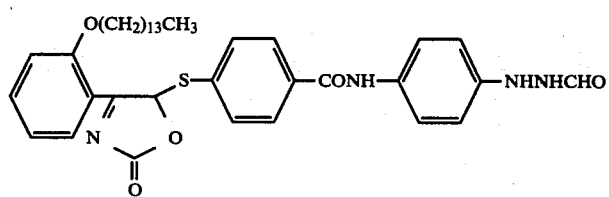
(61)
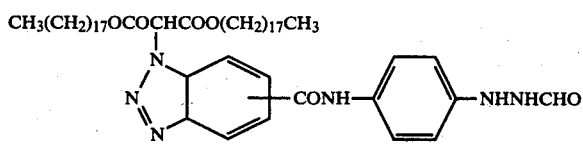
(62)
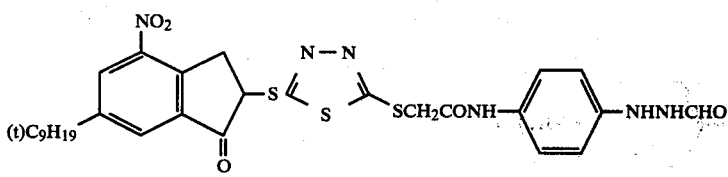
(63)
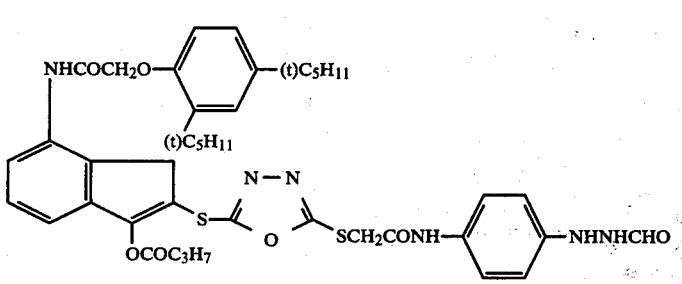
(64)
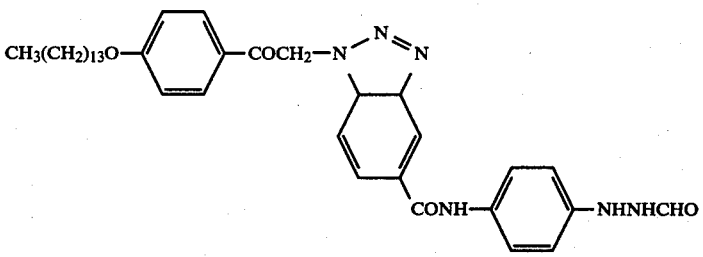
(65)

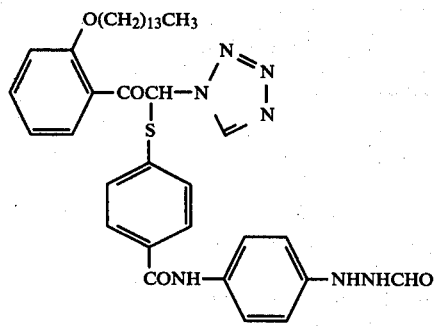

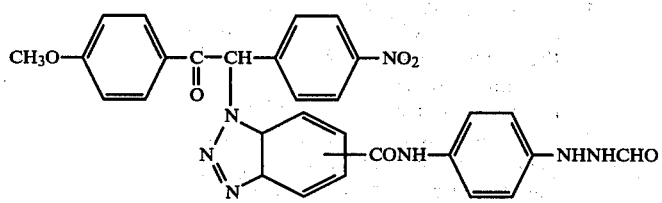

(66)

(67)

-continued

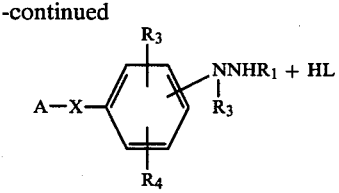

According to synthesis (2), the reaction of obtaining A-L (L represents a coupling-off group such as chlorine, bromine, etc.) by introducing a coupling-off group into the coupler A-H (wherein H as usual, represents a hydrogen atom) is preferably carried out in a halide solvent such as chloroform, methylene chloride, dichloroethane, etc. In this case, bromine, sulfuryl chloride, N-bromosuccinimide, etc. is used as the reacting agent. Thereafter, A-L is allowed to react with

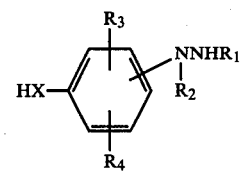

Compounds according to the present invention represented by formula (II) can be synthesized by various synthesis routes. Typical synthesis are illustrated in (1) and (2) below.

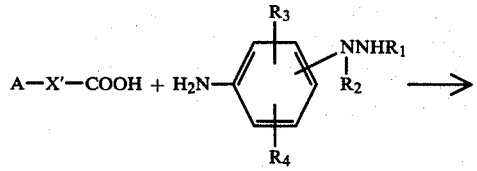

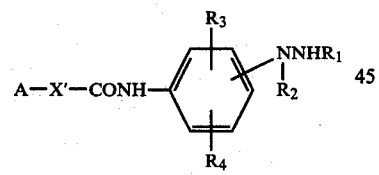

According to synthesis (1), the objective compounds are obtained by condensing couplers having a carboxyl group as a coupling-off group with certain anilines in a solvent such as dimethylformamide, acetonitrile, methylene chloride, tetrahydrofuran, dimethylacetamide, acetone, pyridine, etc., using a condensing agent (for example, N,N'-dicyclohexyl carbodiimide, carbonyldiimidazole, etc.). In the formulae of synthesis (1), X' represents a divalent linking group.

(2)

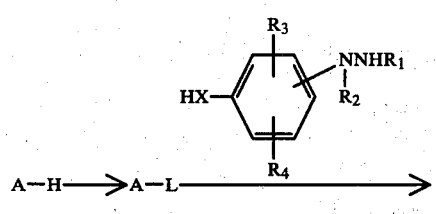

in a solvent such as chloroform, methylene chloride, dichloroethane, dimethylformamide, dimethylacetamide, sulforan, acetonitrile, etc. to obtain the objective compound. In this case, if necessary, bases such as pyridine, triethylamine, sodium hydroxide, potassium hydroxide, DBU (diazabicycloundecene), DBN (diazabicyclononane), etc. may be used.

Examples of synthesis are described below.

Synthesis 1

Synthesis of 1-hydroxy-4-[2-{4-(2-formylhydrazino)anilinocarbonyl-methylthio}ethoxy]-N-n-hexadecyl-2-naphthamide: Compound (1)

To 150 ml of 2-bromoethanol, 60 g (0.3 mol) of 1,4-dihydroxy-2-naphthoic acid was added, and the reaction was carried out at 90° C. with stirring for 2 hours while introducing hydrogen chloride gas. After being cooled (10°-20° C.), precipitated crystals were separated by filtration to obtain 47.4 g (50% yield) of 1-hydroxy-4-(β-bromoethoxy)-2-naphthoic acid.

31 g (0.1 mol) of the resulting naphthoic acid derivative, 16.8 g (0.12 mol) of p-nitrophenol and 2.0 ml of dimethylformamide were added to 800 ml of acetonitrile, and 18.8 g (0.16 mol) of thionyl chloride was added thereto with stirring under refluxing with heat. After carrying out the reaction for 1 hour, the precipitated crystals were separated by filtration to obtain 42.6 g (0.098 mol) (98% yield) of p-nitrophenyl ester of 1-hydroxy-4-(β-bromoethoxy)-2-naphthoic acid.

26 g (0.06 mol) of the resulting p-nitrophenyl ester was heated with stirring together with 17.3 g (0.072 mol) of n-hexadecylamine in 300 ml of acetonitrile. After being stirred for 2 hours, acetonitrile was removed by distillation under a reduced pressure, and the precipitated crystals were separated by filtration to obtain 27 g (83% yield) of 1-hydroxy-4-(β-bromoethoxy)-N-n-hexadecyl-2-naphthamide.

5 g (0.01 mol) of the resulting naphthamide, 2.7 g (0.029 mols) of thioglycolic acid and 2.1 g (0.038 mol) of potassium hydroxide were then added to a mixture of 50 ml of methanol and 10 ml of water and heated to form a solution. After refluxing with heating for 3 hours, 100 ml of water was added. 5 ml of concentrated hydrochloric acid was added thereto while cooling (10°–20° C.) and the precipitated crystals were separated by filtration. They were recrystallized from n-hexane to obtain 4.8 g (88% yield) of 1-hydroxy-4-(β-carboxymethylthioethoxy)-N-n-hexadecyl-2-naphthamide. Melting point: 91°–93° C.

Then, 1-formyl-2-(4-aminophenyl)hydrazide was synthesized according to the process described in Japanese Patent Application (OPI) No. 74729/79. Namely, to 1.6 l of acetonitrile, 459 g of 4-nitrophenylhydrazine was added with stirring, and 322 g of formic acid was then slowly added thereto to obtain a homogeneous solution. After 20 minutes, crystals were precipitated. After carried out the reaction at a temperature of 80° C. for further 2 hours, the mixture was cooled and filtered to separate crystals. The crystals were washed with acetonitrile and dried to obtain 495 g of 1-formyl-2-(4-nitrophenyl)hydrazide. Melting point: 184°–186° C.

30 g of 1-formyl-2-(4-nitrophenyl)hydrazine was then catalytically reduced at a room temperature in 1.6 l of ethanol using palladium-carbon as a catalyst. The reacting solution was filtered, and the filtrate was evaporated to dryness to obtain 20.5 g of white solid: 1-formyl-2-(4-aminophenyl)hydrazide. Melting point: 123°–125° C.

5.5 g (0.01 mol) of 1-hydroxy-4-(β-carboxymethylthioethoxy)-N-n-hexadecyl-2-napthamide and 1.5 g (0.01 mol) of 1-formyl-2-(4-aminophenyl)hydrazide were dissolved in 20 ml of dimethylformamide, and a solution of 2.1 g (0.01 mol) of N,N'-dicyclohexylcarbodiimide in 10 ml of acetonitrile was added dropwise thereto with stirring at a room temperature. After being added dropwise, the mixture was stirred at the room temperature for 2 hours and the formed N,N'-dicyclohexyl urea was separated by filtration. To the filtrate, 100 ml of water was added, and the product was extracted with ethyl acetate. The ethyl acetate layer was taken out. After ethyl acetate was removed by distillation, recrystallization was carried out by adding 50 ml of methanol to obtain 6.0 g (88% yield) of the Compound (1). Melting point: 174°–178° C.

| Elementary analysis: ($C_{38}H_{54}N_4O_5S$) | | |
|---|---|---|
| H % | C % | N % |
| Calc'd 8.02 | 67.23 | 8.25 |
| Found 8.02 | 67.17 | 8.34 |

Synthesis 2

Synthesis of 1-hydroxy-4-{4-(2-formylhydrazino)anilinocarbonylmethyloxy}-N-(3-n-dodecyloxypropyl)-2-naphthamine: Compound (3).

To 700 ml of dimethylformamide, 249 g (1.22 mol) of 1,4-dihydroxy-2-naphthoic acid was added, and the mixture was stirred under a nitrogen atmosphere. To the mixture, 490 ml (2.44 mols) of a 28% solution of sodium methoxide in methanol was added dropwise over 20 minutes. After 10 minutes, 150 g (1.22 mol) of ethyl chloroacetate was added dropwise over 30 minutes, and the mixture was stirred for 3 hours while keeping the temperature at 50° C. The reaction solution was poured into a mixture of 160 ml of concentrated chloric acid and 5 l of iced water, and the precipitated crystals were filtered off and dried to obtain 335 g (95% yield) of 1-hydroxy-4-ethoxycarbonylmethyloxy-2-naphthoic acid.

335 g (1.15 mol) of 1-hydroxy-4-ethoxycarbonylmethyloxy-2-naphthoic acid and 160 g (1 mol) of p-nitrophenol were added to 1 liter of toluene, and the mixture was stirred while keeping the temperature at 80° C. 130 mols of thionyl chloride were added dropwise over 30 minutes. After stirring for 30 minutes more, the mixture was cooled. The precipitated crystals were filtered off and dried to obtain 271 g (57% yield) of 1-hydroxy-4-ethoxycarbonylmethyloxy-2-naphthoic acid 4-nitrophenyl ester. Melting point: 165°–167° C.

271 g (0.66 mol) of 1-hydroxy-4-ethoxycarbonylmethyloxy-2-naphthoic acid 4-nitrophenyl ester and 160 g (0.66 mol) of 3-n-dodecyloxypropylamine were added to 750 ml of tetrahydrofuran, and the mixture was stirred for 3 hours. 2 liters of water were added to the reacting solution, and extraction was carried out with 1 liter of ethyl acetate. After removal of ethyl acetate by distillation, the residue was dissolved in 1 liter of methanol, and cooled. The precipitated crystals were filtered off and dried to obtain 205 g (66% yield) of 1-hydroxy-4-ethoxy-carbonylmethyloxy-N-(3-n-dodecyloxypropyl)-2-naphthamide. Melting point: 66°–67.5° C.

205 g (0.4 mol) of 1-hydroxy-4-ethoxycarbonylmethyloxy-N-(3-n-dodecyloxypropyl)2-naphthamide was dispersed in 600 ml of methanol at the room temperature. A solution containing 105 g of potassium hydroxide in 250 ml of methanol was added slowly with stirring, followed by stirring for 1 hour. After being neutralized by adding concentrated hydrochloric acid, the precipitated crystals were filtered off and dried to obtain 184 g (94% yield) of 1-hydroxy-4-carboxymethyloxy-N-(3-n-dodecyloxypropyl)2-naphthamide. Melting point: 150° C.

The reaction of 71.5 g (0.147 mol) of 1-hydroxy-4-carboxymethyloxy-N-(3-n-dodecyloxypropyl)-2-naphthamide with 22.2 g (0.147 mol) of 1-formyl-2-(4-aminophenyl)hydrazide was carried out by the same manner as in Synthesis 1 with using N,N'-dicyclohexylcarbodiimide, and the final product was recrystallized from methanol to obtain 68.3 g (75% yield) of Compound (3). Melting point: 137°–141° C.

Elementary analysis:
(C$_{35}$H$_{48}$N$_4$O$_6$)

|  | H % | C % | N % |
|---|---|---|---|
| Calc'd | 7.79 | 67.71 | 9.02 |
| Found | 7.80 | 67.55 | 8.87 |

Synthesis 3

Synthesis of 1-(2,4,6-trichlorophenyl)-3-(2-chloro-5-tetradecanamido)anilino-4-[2-{4-(2-formylhydrazino)anilinocarbonyl}ethylthio]-2-pyrazolin-5-one: Compound (29).

1-(2,4,6-Trichlorophenyl)-3-(2-chloro-5-tetradecanamido)anilino-4-(2-carboxyethylthio)-2-pyrazolin-5-one was synthesized according to the process described in Japanese Patent Application (OPI) No. 29805/80.

Under a nitrogen atmosphere, 45 g of 1-(2,4,6-trichlorophenyl)-3-(2-chloro-5-tetradecanamido)anilino-2-pyrazolin-5-one and 7.6 g of thiourea were dissolved in 250 ml of dimethylformamide. 16 g of bromine was added dropwise thereto at 10° C. or less. To the resulting solution, a solution obtained by dissolving 25 g of potassium hydroxide in 120 ml of methanol was added. The reacting temperature was gradually raised to room temperature, and the mixture was stirred for 1 hour. Thereafter, 20 g of β-bromopropionic acid was added, and the mixture was stirred for 2 hours. After adding 1 liter of ethyl acetate, the reacting solution was transferred into a separatory funnel and washed with 1 liter of water. After washed with 1 N diluted hydrochloric acid, it was additionally washed two times with 1 liter of water. The ethyl acetate solution was condensed and cooled to precipitate crystals. The crystals were filtered off and dried to obtain 40.0 g (76%) of 1-(2,4,6-trichlorophenyl)-3-(2-chloro-5-tetradecanamido)anilino-4-(2-carboxyethylthio)-2-pyrazoline-5-one. Melting point: 185°–187° C.

7.2 g (0.01 mol) of 1-(2,4,6-trichlorophenyl)-3-(2-chloro-5-tetradecanamido)anilino-4-(2-carboxyethylthio)-2-pyrazolin-5-one and 1.5 g (0.01 mol) of 1-formyl-2-(4-aminophenyl)hydrazide were processed by the same manner as in Synthesis 1 using N,N'-dicyclohexylcarbodiimide, and the resulting final product was developed by a chromatographic column filled with silica gel. The developing solution was evaporated to dryness to obtain 5.5 g (65% yield) of white solid Compound (29).

Elementary analysis:
(C$_{39}$H$_{47}$N$_7$O$_4$SCl$_4$)

|  | H % | C % | N % |
|---|---|---|---|
| Calc'd | 5.56 | 54.00 | 11.51 |
| Found | 5.51 | 53.74 | 11.32 |

Synthesis 4

Synthesis of α-pivaloyl-α-(4'-(4''-formylhydrazinoanilinocarbonyl)phenoxy)-2-chloro-5-(n-hexadecanesulfonamido)acetanilide: Compound (50).

α-Pivaloyl-60-(4-carboxyphenoxy)-2-chloro-5-(n-hexadecanesulfonamido)acetanilide was synthesized according to the process described in U.S. Pat. No. 3,408,194. Melting point: 121°–124° C.

7.2 g (0.01 mol) of α-pivaloyl-α-(4-carboxyphenoxy)-2-chloro-5-(n-hexadecanesulfonamido)acetanilide and 1.5 g (0.01 mol) of 1-formyl-2-(4-aminophenyl)hydrazide were subjected to reacting by the same manner as in Synthesis 1 using N,N'-dicyclohexylcarbodiimide, and the resulting crude product was recrystallized from acetonitrile to obtain 3.6 g (42% yield) of Compound (50). Melting point: 140°–142° C.

Elementary analysis:
(C$_{43}$H$_{60}$N$_5$O$_7$ClS)

|  | H % | C % | N % |
|---|---|---|---|
| Calc'd | 7.31 | 62.48 | 8.47 |
| Found | 7.28 | 62.66 | 8.42 |

Synthesis 5

Synthesis of α-[5-{4-(2-formylhydrazino)anilinocarbonyl}benzotriazo-1-yl]octadecylmalonate: Compound (62).

15.2 g (0.01 mol) of 3,4-diaminobenzoic acid was dissolved in a mixed solvent composed of 100 ml of acetic acid and 50 ml of water. The solution was cooled to less than 5° C., and a solution prepared by dissolving 10 g (0.14 mol) of sodium nitrite in 30 ml of water was added dropwise with stirring. After the mixture was stirred at a room temperature for 2 hours, the precipitated crystal was filtered off. It was recrystallized from methanol to obtain 5-carboxybenzotriazole 11.7 g (72% yield). Melting point 300° C. (decomposition).

8.2 g (0.05 mol) of 5-carboxybenzotriazole was dissolved in 50 ml of dimethylformamide. With stirring at room temperature, a solution prepared by dissolving 10.3 g of N,N'-dicyclohexylcarbodiimide in 20 ml of acetonitrile was added dropwise. After stirring for 2 hours, the precipitate formed was removed by filtration, and 50 ml of water was added to the filtrate to obtain precipitate. The precipitate was filtered off and recrystallized form ethanol to obtain 8.9 g (60% yield) of 5-{4-(2-formylhydrazino)anilinocarbonyl}benzotriazole. Melting point: 241°–243° C. (decomposition).

60.9 g of octadecyl malonate was dissolved in 500 ml of chloroform, and the solution was cooled to 5° C. or less. With stirring, 16 g of bromine was added dropwise. After stirring for 30 minutes more, the reacting solution was transferred into a separatory funnel and washed three times with 500 ml of water. The chloroform layer was taken out and chloroform was removed by distillation. The resulting residue was recrystallized from ethyl acetate to obtain 61.3 g (89% yield) of α-bromooctadecyl malonate. Melting point: 48° C.

8.9 g (0.03 mol) of 5-{4-(2-formylhydrazino)anilinocarbonyl}benzotriazole and 3.0 g of triethylamine were added to 50 ml of dimethylformamide. With stirring at room temperature, a solution prepared by dissolving 20.6 g of α-bromooctadecyl malonate in 50 ml of dimethylformamide was added dropwise over 1 hour. After stirring for further 5 hours, the reacting solution was transferred into a separatory funnel and extracted by adding 200 ml of ethyl acetate and 200 ml of water. The ethyl acetate layer was washed twice with 200 ml of water and, thereafter, ethyl acetate was removed by distillation. The residue was developed by a chromatographic column filled with silica gel and the developing solution was evaporated to dryness to obtain white solid Compound (62).

| Elementary analysis: (C$_{53}$H$_{86}$N$_6$O$_6$) | | | |
|---|---|---|---|
| | H % | C % | N % |
| Calc'd | 9.60 | 70.47 | 9.30 |
| Found | 9.74 | 70.51 | 9.28 |

The compounds of the present invention exhibit the following effects, either in the case of being used alone, or in the case of being used together with other color couplers, because a diffusable development accelerator released by a coupling reaction with an oxidation product of the developing agent accelerates development of silver halide grains having a low developing rate.

(i) When comparison is carried out at the same exposure, the density increases as compared with the case of using conventional couplers.

(ii) The density of the fogged part increases less, because the amount of the development accelerator released is small.

(iii) The developing rate becomes high. On the basis of these effects, highly sensitive hard gradations can be obtained. Obtaining the hard gradation is proof of the fact that the development accelerator imagewise functions. This fact of obtaining highly sensitive hard gradation is effective for improving the qualities of images, particularly granularity, by combining with a low-sensitive microgranular emulsion, by combining with a coupler having low activity, or by combining with a development inhibiting substance or a development inhibitor precursor.

Further, the fact that the developing rate is high is useful for rapid processing. In the multilayer color sensitive materials, it is well known that the development reaction is retarded by permeation of the developing solution into the lower layer part and by diffusion of the development inhibiting substance from the upper layer part. However, the compounds of the present invention exhibit a particularly remarkable development accelerating function when used in such sensitive materials.

Furthermore, since the couplers of the present invention have a great effect of reducing the amount of silver halide grains which are not developed even if developed for a sufficiently long time, the so-called "dead grain", the amount of silver used is remarkably reduced in color sensitive materials using a large amount of silver.

The couplers of the present invention can be utilized for any processing by using conventional silver halide color sensitive materials such as color negative films, color paper, color positive films, color reversal films for slides, color reversal films for cinema or color reversal films for televisions, etc. However, they are particularly effective for color negative films and color reversal films requiring high sensitivity and high quality images.

In view of the high price of silver, which is the raw material for photographic light-sensitive materials, it is an important matter to reduce the amount of silver used for the photographic light-sensitive materials. From this point of view, it has been proposed to change X-ray films using a large amount of silver into dye utilization films (black coupler process described in U.S. Pat. Nos. 3,622,629, 3,734,735 and 4,126,461 and Japanese Patent Application (OPI) Nos. 42725/77, 105247/80 and 105248/80; and the three color coupler mixing process described in *Research Disclosure* No. 17123 (July, 1978)). The couplers of the present invention are very useful for these light-sensitive materials, because silver halide can be effectively used and the rapid processing can be carried out.

The photographic emulsion layers in the photographic light-sensitive materials of the present invention may contain color forming couplers, namely, compounds capable of coloring by an oxidation coupling reaction with the aromatic primary amine developing agent (for example, phenylenediamine derivatives, aminophenol derivatives, etc.) in the color development processing. For example, there are 5-pyrazolone couplers, pyrazolobenzimidazole couplers, cyanoacetyl coumarone couplers, ring-opened acylacetonitrile couplers, etc. as magenta couplers; acylacetamide couplers (for example, benzoylacetanilides and pivaloylacetanilides), etc. as yellow couplers; and naphthol couplers, phenol couplers, etc. as cyan couplers. It is preferred that these couplers have a hydrophobic group (called a ballast group) in the molecule, or are nondiffusible polymers. The couplers may be any 2-equivalent ones and 4-equivalent ones to silver ion. Further, the couplers may be colored couplers having a function of color correction or couplers which release a development inhibitor by development (the so-called DIR couplers).

Further, the emulsion layers may contain noncoloring DIR coupling compounds which release a development inhibitor, the product of which formed by a coupling reaction is colorless, other than DIR couplers.

The emulsion layers may contain noncoloring couplers the product of which formed by a coupling reaction is colorless, infrared couplers which form a dye having an infrared absorption by a coupling reaction, and black forming couplers which form black images by a coupling reaction, etc. other than the above described couplers.

Examples of the magenta couplers include those described in U.S. Pat. Nos. 2,600,788, 2,983,608, 3,062,653, 3,127,267, 3,311,476, 3,419,391, 3,519,429, 3,558,319, 3,582,322, 3,615,506, 3,834,908, 3,891,445, 3,926,631, 3,928,044, 4,076,533, 4,189,321 and 4,220,470, German Pat. No. 1,810,464, German Patent Application (OLS) Nos. 2,408,665, 2,417,945, 2,418,959, 2,424,467, 2,536,191, 2,651,363, 2,935,848 and 2,944,601, Japanese Patent Publication Nos. 6031/65, 38498/79, 10901/80, 29420/80 and 29421/80, and Japanese Patent Application (OPI) Nos. 74027/74, 129538/74, 60233/75, 159336/75, 20826/76, 26541/76, 36938/76, 105820/76, 42121/77, 58922/77, 9122/78, 55122/78, 48540/79, 80744/79, 62454/80, 118034/80, etc.

Examples of the yellow couplers include those described in U.S. Pat. Nos. 2,875,057, 3,265,506, 3,408,194, 3,551,155, 3,582,322, 3,725,072, 3,891,445, 3,894,875, 3,973,968, 3,990,896, 4,008,086, 4,012,259, 4,022,620, 4,029,508, 4,046,575, 4,057,432, 4,059,447, 4,095,983, 4,133,958, 4,157,919, 4,182,630, 4,186,019, 4,203,768 and 4,206,278, German Pat. No. 1,547,868, German Patent Application (OLS) Nos. 2,213,461, 2,219,917, 2,261,361, 2,263,875, 2,414,006, 2,528,638, 2,935,849 and 2,936,842 British Patent 1,425,020, Japanese Patent Publication Nos. 13576/74, 10783/76, 36856/79 and 13023/80, Japanese Patent Application (OPI) Nos. 26133/72, 66835/73, 6341/75, 34232/75, 87650/75, 130442/75, 75521/76, 102636/76, 145319/76, 21827/76, 82424/77, 115219/77, 48541/79, 121126/79, 2300/80, 36900/80, 38576/80 and 70841/80, *Research Disclosure* No. 18053, etc.

Examples of the cyan couplers include those described in U.S. Pat. Nos. 2,369,929, 2,434,272, 2,474,293, 2,521,908, 2,895,826, 3,034,892, 3,311,476, 3,458,315, 3,476,563, 3,583,971, 3,591,383, 3,758,308, 3,767,411, 4,004,929, 4,052,212, 4,124,396, 4,146,396 and 4,205,990, German Patent Application (OLS) Nos. 2,214,489, 2,414,830, 2,454,329, 2,634,694, 2,841,166, 2,934,769, 2,945,813, 2,947,707 and 3,005,355, Japanese Patent Publication Nos. 37822/79 and 37823/79, and Japanese Patent Application (OPI) Nos. 5055/73, 59838/73, 130441/75, 26034/76, 146828/76, 69624/77, 90932/77, 52423/78, 105226/78, 110530/78, 14736/79, 48237/79, 66129//79, 131931/79, 32071/80, 65957/80, 73050/80, 108662/80, etc.

Examples of the colored couplers include those described in U.S. Pat. Nos. 2,521,908, 3,034,892 and 3,476,560, German Patent Application (OLS) No. 2,418,959, Japanese Patent Publication Nos. 22335/63, 11304/67, 2016/69 and 32461/69, and Japanese Patent Application (OPI) Nos. 26034/76, 42121/77, etc.

Examples of the DIR couplers include those described in U.S. Pat. Nos. 3,227,554, 3,617,291, 3,632,345, 3,701,783, 3,790,384, 3,933,500, 3,938,996, 4,052,213, 4,157,916, 4,171,223, 4,183,752, 4,187,110 and 4,226,834, German Patent Application (OLS) Nos. 2,414,006, 2,454,301, 2,454,329, 2,540,959, 2,707,489, 2,709,688, 2,730,824, 2,754,281, 2,835,073, 2,853,362, 2,855,697 and 2,902,681, British Pat. No. 953,454, Japanese Patent Publication Nos. 16141/76, 2776/78 and 34933/80, Japanese Patent Application (OPI) Nos. 122335/74, 69624/77, 154631/77, 7232/78, 9116/78, 15136/78, 20324/78, 29717/78, 13533/78, 143223/79, 73033/79, 114241/79, 115229/79, 145135/79, 84935/80 and 135835/80, and Research Disclosure No. 18104 (May, 1979), etc.

In addition to DIR couplers, the light-sensitive materials may contain compounds which release a development inhibitor by development, examples of which include those described in U.S. Pat. Nos. 3,297,445 and 3,379,529, German Patent Application (OLS) No. 2,417,914 and Japanese Patent Application (OPI) Nos. 15271/77 and 9116/78.

Examples of the noncoloring couplers include those described in U.S. Pat. Nos. 3,912,513 and 4,204,867 and Japanese Patent Application (OPI) No. 152721/77, etc.

Examples of the infrared couplers include those described in U.S. Pat. No. 4,178,183, Japanese Patent Application (OPI) No. 129036/78, and Research Disclosure No. 13460 and No. 18732 (Nov., 1979).

Examples of the black forming couplers include those described in U.S. Pat. Nos. 4,126,461, 4,137,080, and 4,200,466, and Japanese Patent Application (OPI) No. 46029/78, 133432/78, 105247/80 and 105247/80, etc.

The emulsion layers in the photographic light-sensitive materials of the present invention may contain polymeric couplers. Examples of these couplers include those described in U.S. Pat. Nos. 2,698,797, 2,759,816, 2,852,381, 3,163,625, 3,208,977, 3,211,552, 3,299,013, 3,370,952, 3,424,583, 3,451,820, 3,515,557, 3,767,412, 3,912,513, 3,926,436, 4,080,211, 4,128,427 and 4,215,195, and Research Disclosure: No. 17825, No. 18815 and No. 19033.

The compounds of the present invention may used alone, or they may be used together with other couplers. Particularly, in the case of using them together with a coupler having low activity in the latter process, the granularity is remarkably improved as compared with the case of using the coupler having high activity alone. Examples of couplers suitably used together with the compounds of the present invention are described below. Magenta couplers:

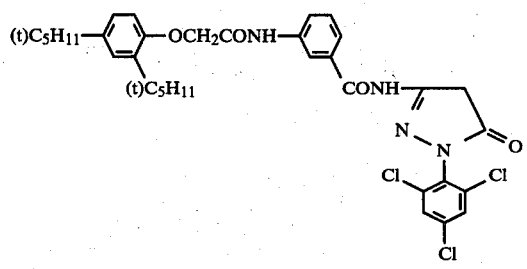

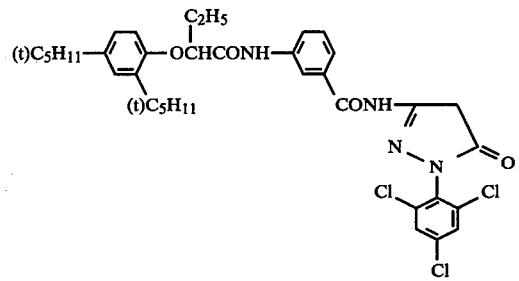

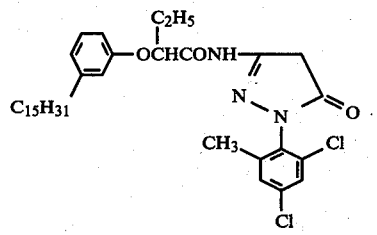

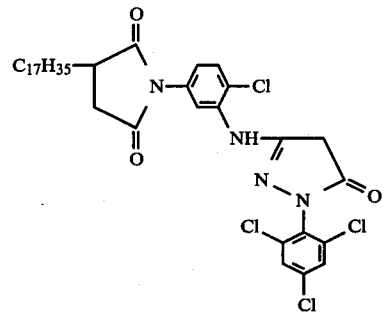

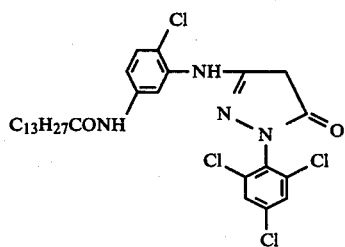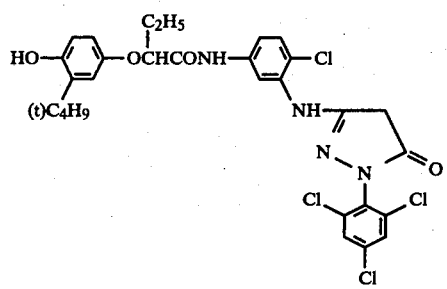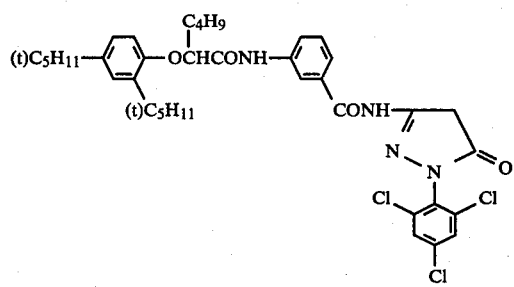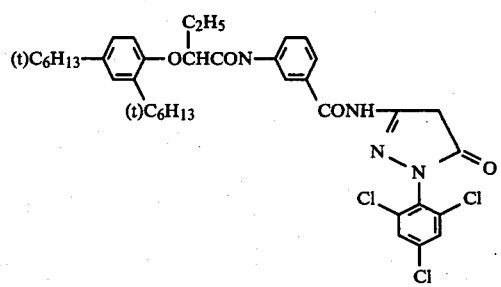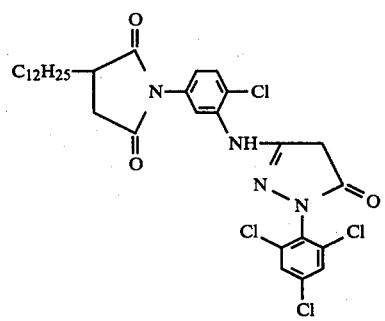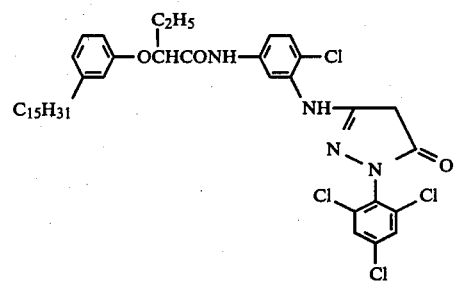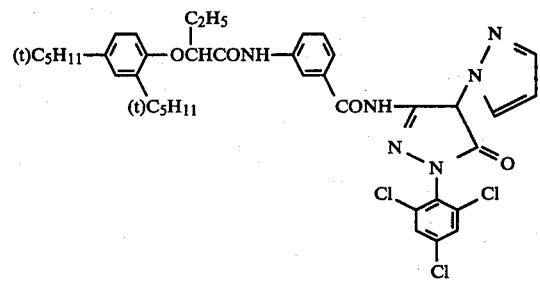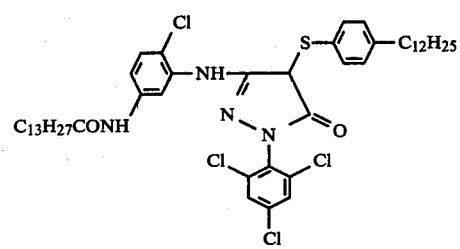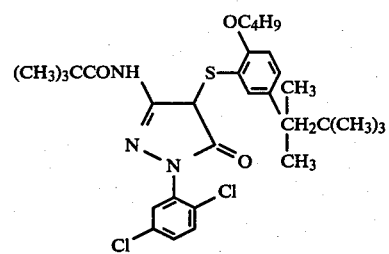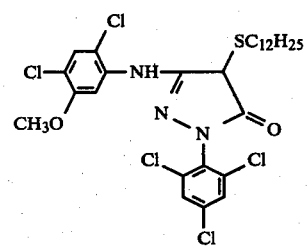

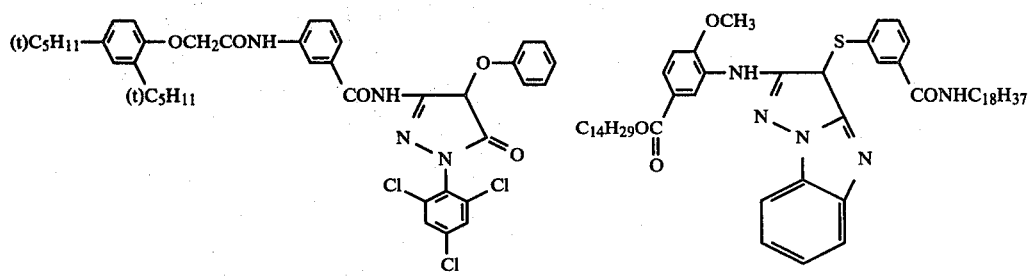
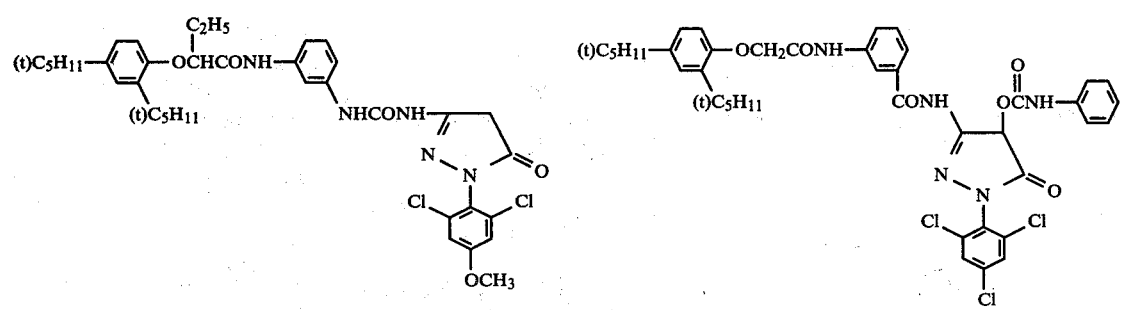
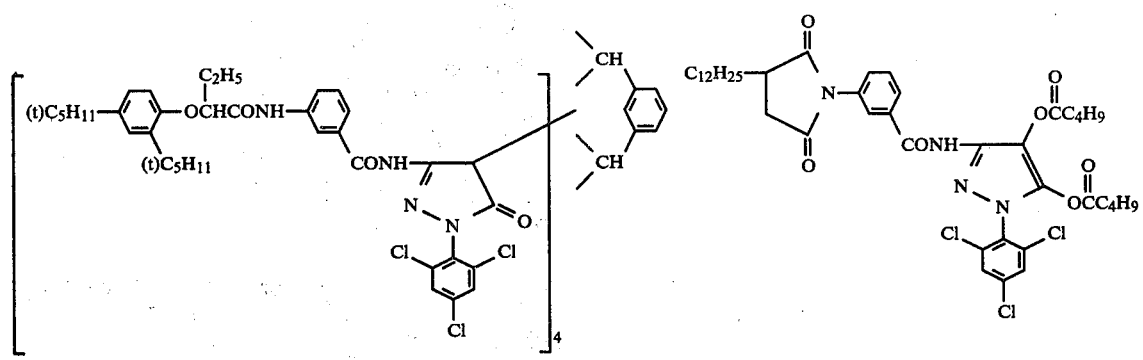
Yellow Couplers
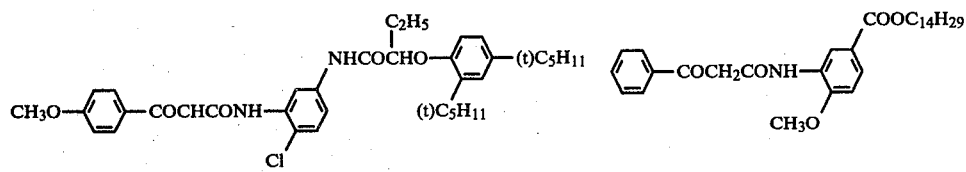

-continued
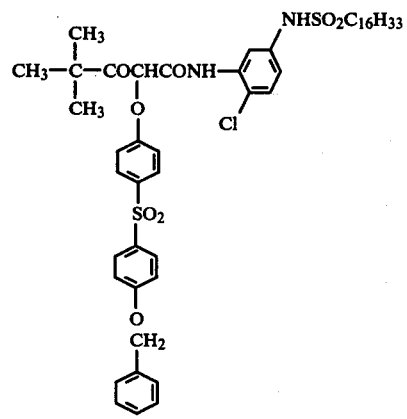
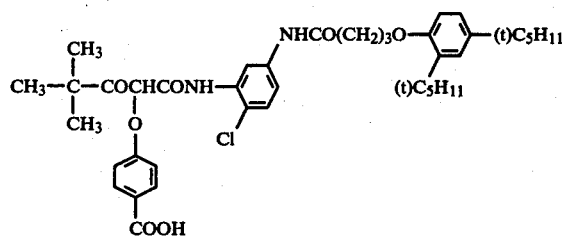
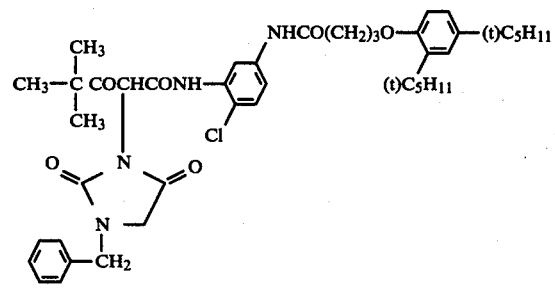
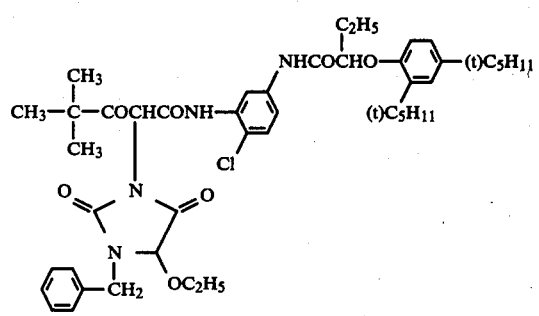
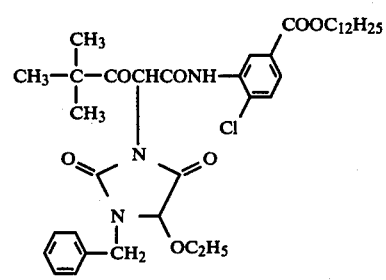
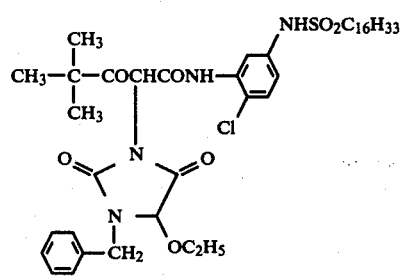
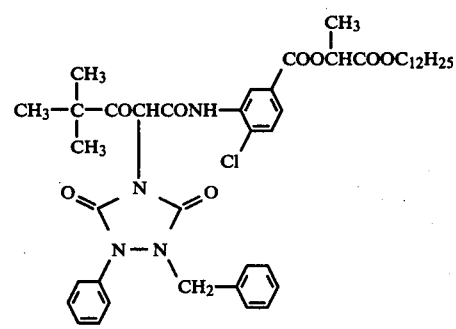
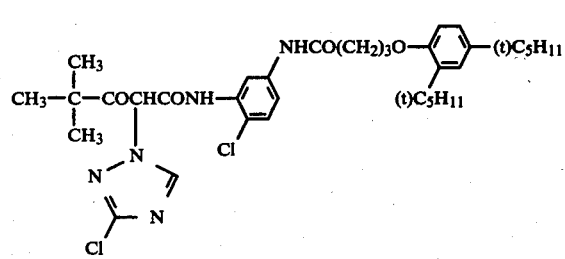
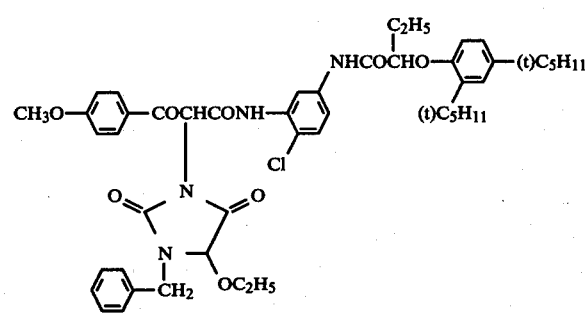
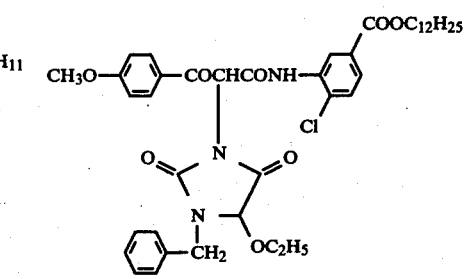

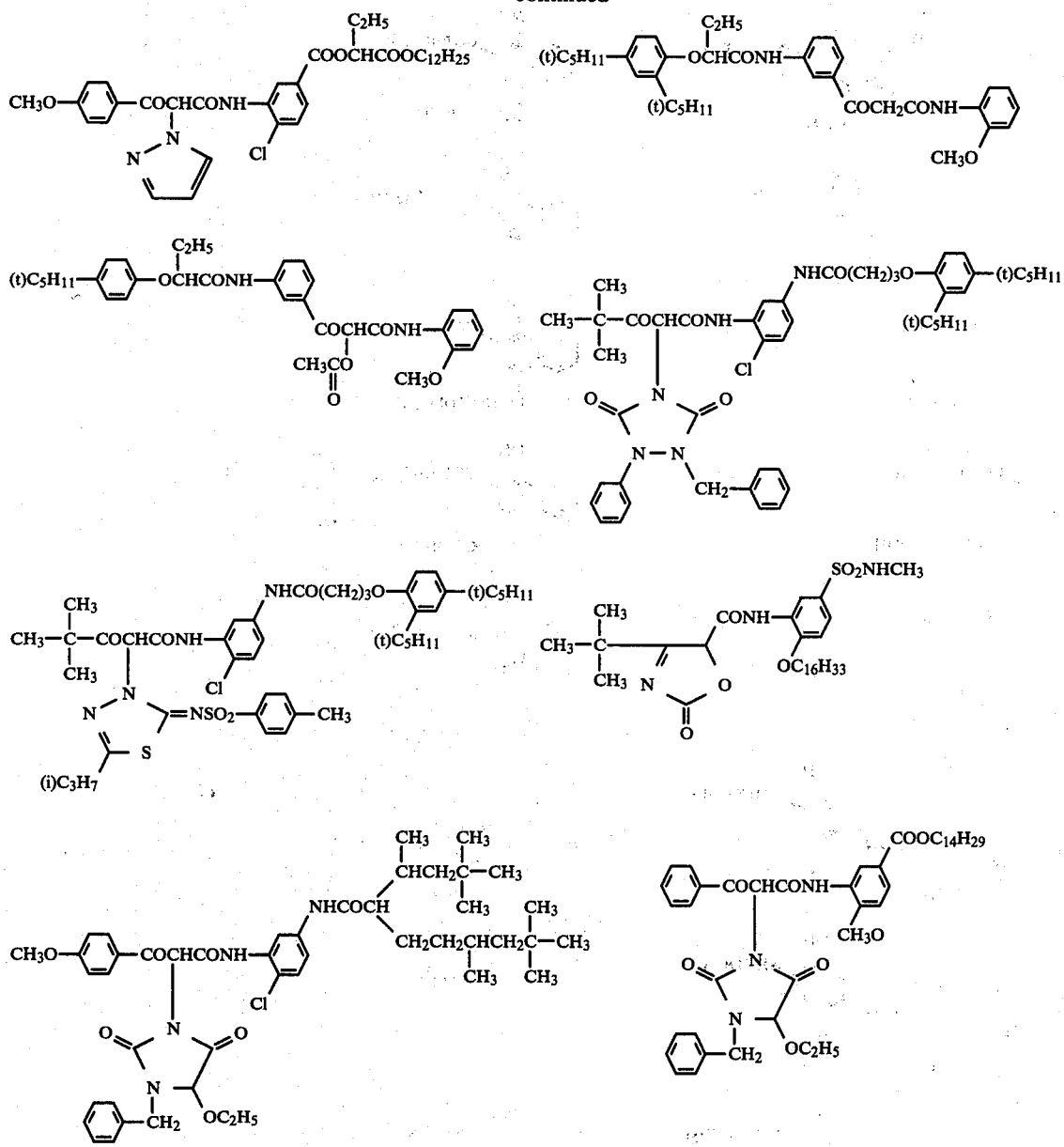
Cyan Couplers
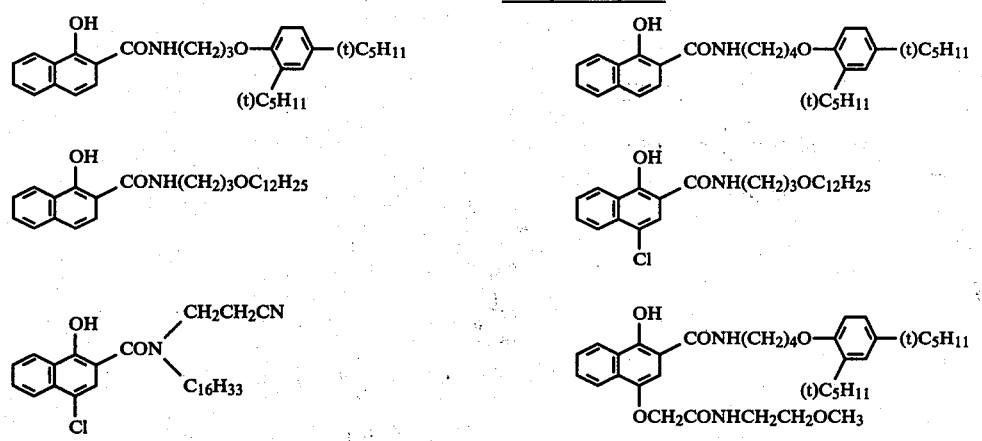

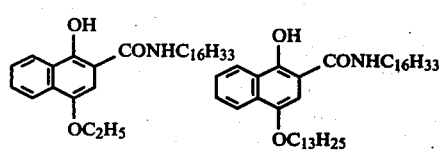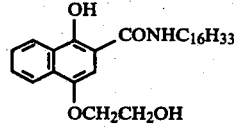
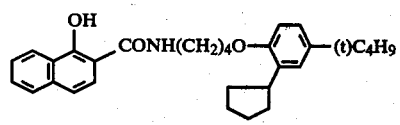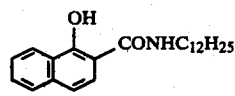
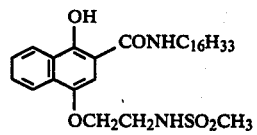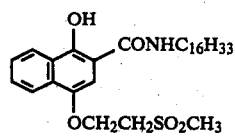
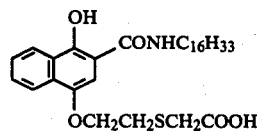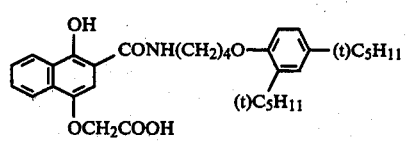
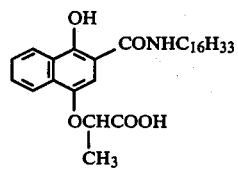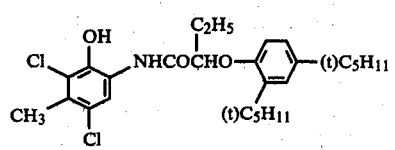
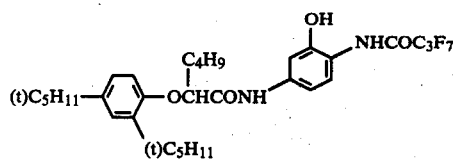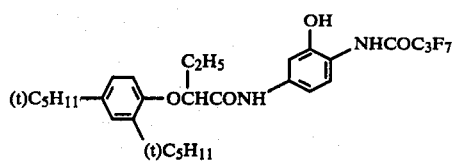
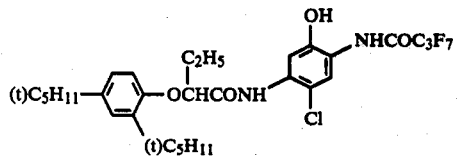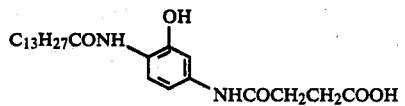
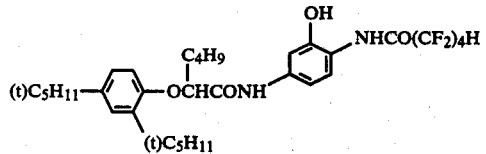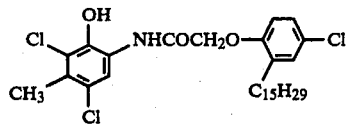
DIR Couplers
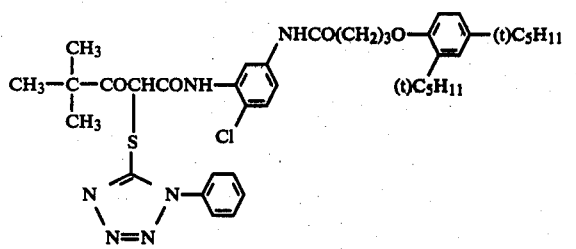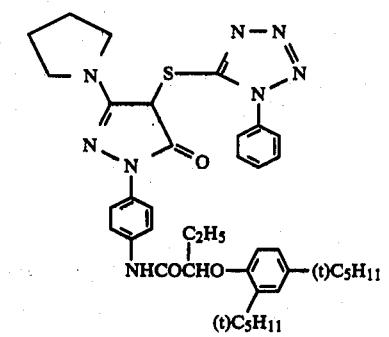

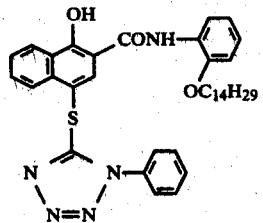
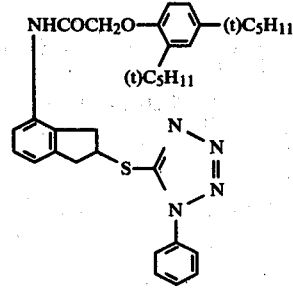
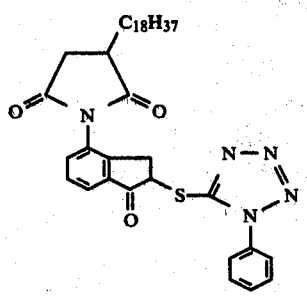
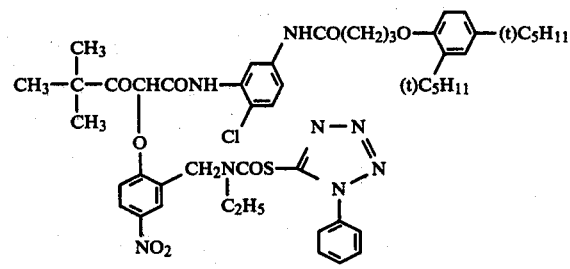
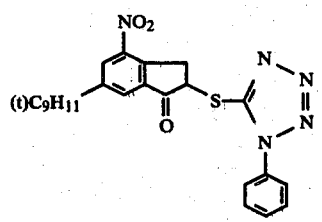
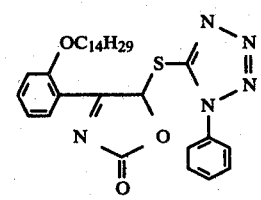
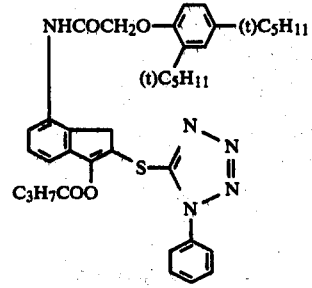
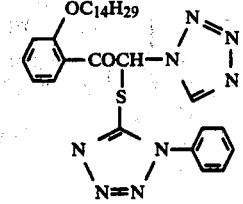
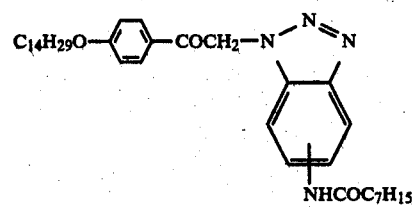
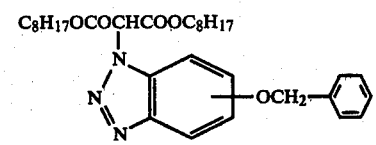
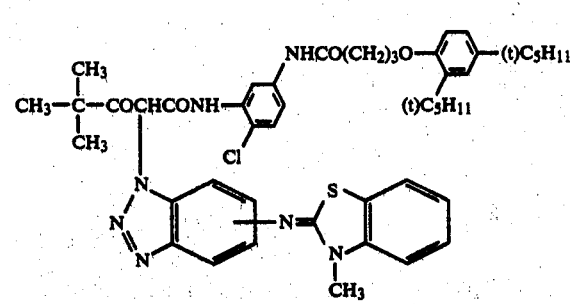
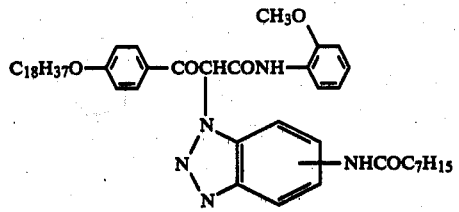

-continued
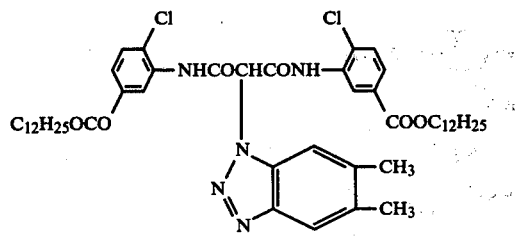
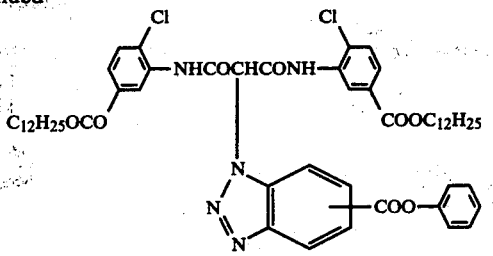
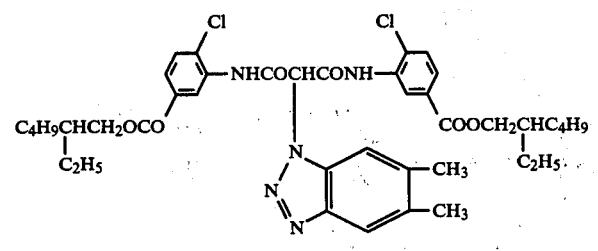
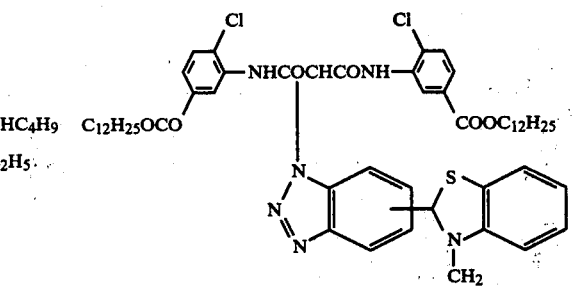
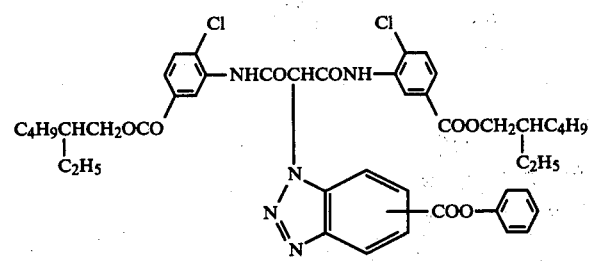
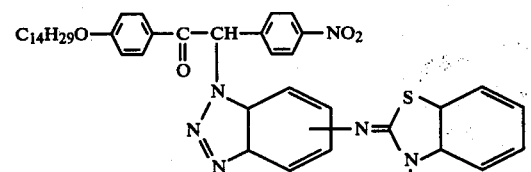
Black-Colored Couplers
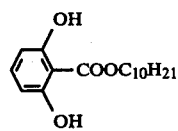
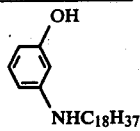
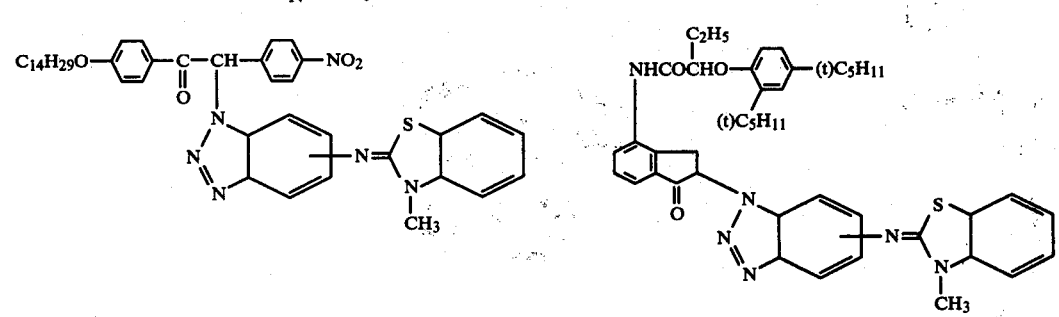
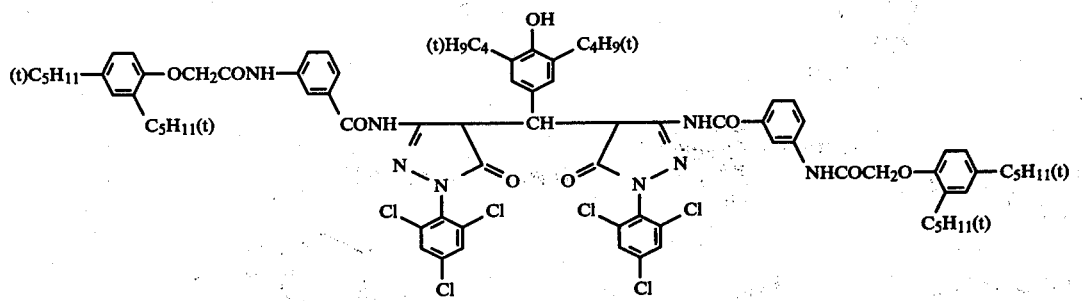
In order to introduce the compounds of the present invention into the silver halide emulsion layers, known processes such as a process described in U.S. Pat. No. 2,322,027 are used. For example, they are dispersed in a hydrophilic colloid after dissolved in alkyl phthalates (dibutyl phthalate, dioctyl phthalate, dicyclohexyl phthalate, etc.), phosphoric acid esters (diphenyl phosphate, triphenyl phosphate, tricresyl phosphate, dioctylbutyl phosphate, trioctyl phosphate, trihexyl phosphate, tricyclohexyl phosphate, etc.), citric acid esters (for example, tributyl acetylcitrate), benzoic acid esters (for example, octyl benzoate), alkylamides (for example, diethyl laurylamide), aliphatic acid esters (for example, dibutoxyethyl succinate and dioctyl azelate), trimesic acid esters (for example, tribytyl trimesate), etc. or organic solvents having a boiling point of about 30° C. to 150° C., for example, lower alkyl acetate such as ethyl acetate or butyl acetate, ethyl propionate, secondary butyl alcohol, methyl isobutyl ketone, β-ethoxyethyl acetate, methyl cellosolve, etc. The above described high boiling point organic solvents and low boiling point organic solvents may be used as a mixture thereof.

Further, it is possible to use a dispersion process using polymers described in Japanese Patent Publication No. 39853/76 and Japanese Patent Application (OPI) No. 59943/76.

In the case that the compounds of the present invention have acid groups such as a carboxylic acid group or a sulfonic acid group, they are introduced into the hydrophilic colloids as an aqueous alkaline solution.

In the photographic light-sensitive materials of the present invention, the photographic emulsion layers and other layers are applied to flexible bases such as plastic films, paper, cloth, etc. or rigid bases such as glass, ceramics, metal, etc., which are conventionally used for photographic light-sensitive materials. Examples of useful flexible bases include films composed of semisynthetic or synthetic high molecular materials such as cellulose nitrate, cellulose acetate, cellulose acetate butyrate, polystyrene, polyvinyl chloride, polyethylene terephthalate, polycarbonate, etc. and papers coated or laminated with barita, α-olefin polymers (for example, polyethylene, polypropylene or ethylene/butene copolymer), etc. The bases may be colored by dyes or pigments. They may have a black color for the purpose of light-shielding. The surface of these bases is generally subjected to an undercoating treatment in order to improve adhesion to the photographic emulsion layer, etc. The surface of the bases may be subjected to corona discharging, ultraviolet ray application, flame treatment, etc., prior to or after the undercoating treatment.

The present invention can be applied to multilayer multicolor photographic materials having at least two different spectral sensitivities. The multilayer technicolor photographic materials have generally at least one red-sensitive emulsion layer, at least one green-sensitive emulsion layer and at least one blue-sensitive emulsion layer on a base. The order of superposition of these layers can be suitably varied. It is ordinary the case that the red-sensitive emulsion layer contains a cyan coupler, the green-sensitive emulsion layer contains a magenta coupler and the blue-sensitive emulsion layer contains a yellow coupler. However, if necessary, other combinations may be utilized.

In carrying out preparation of emulsions, removal of soluble salts from the emulsions after formation of precipitation or physical ageing may be carried out by a noodle washing method in which gelatin is gelated, or a flocculation method utilizing inorganic salts, anionic surface active agents, anionic polymers (for example, polystyrenesulfonic acid), or gelatin derivatives (for example, acylated gelatin, carbamoylated gelatin, etc.).

The silver halide emulsions are generally chemically sensitized. In order to carry out chemical sensitization, it is possible to use processes as described in *Die Grundlagen der Photographischen Prozesse mit Silberhologeniden*, edited by H. Frieser (Akrdemische Verlagsgesellschaft 1968) pages 675–734.

Namely, it is possible to use a sulfur sensitization process which comprises using sulfur containing compounds capable of reacting with active gelatin and silver (for example, thiosulfates, thioureas, mercapto compounds or rhodanines), a reduction sensitization process which comprises using reducing substances (for example, stannous salts, amines, hydrazine derivatives, formamidinesulfinic acid and silane compounds) and a noble metal sensitization process which comprises using noble metal compounds (for example, gold complex salts and complex salts of metals belonging to Group VIII in the periodic table, such as Pt, Ir, Pd, etc.), which may be used alone or as a combination thereof.

Examples of the sulfur sensitization process have been described in U.S. Pat. Nos. 1,574,944, 2,410,689, 2,278,947, 2,728,668 and 3,656,955, those of the reduction sensitization process have been described in U.S. Pat. Nos. 2,983,609, 2,419,974 and 4,054,458, and those of the noble metal sensitization process have been described in U.S. Pat. Nos. 2,399,083 and 2,448,060 and British Pat. No. 618,061, etc.

As the binder or the protective colloid for the photographic emulsions of the photographic light-sensitive materials of the present invention, gelatin is advantageously used, but other hydrophilic colloids can be used.

For example, it is possible to use proteins such as gelatin derivatives, graft polymers of gelatin and other high molecules, albumin, casein, etc., saccharides such as cellulose derivatives such as hydroxyethyl cellulose, carboxymethyl cellulose, cellulose sulfate, etc., sodium alginate, starch derivatives, etc., and various synthetic hydrophilic high molecular substances such as homopolymers or copolymers, for example, polyvinyl alcohol, polyvinyl alcohol semiacetal, poly-N-vinylpyrrolidone, polyacrylic acid, polymethacrylic acid, polyacrylamide, polyvinylimidazoke, polyvinylpyrazole, etc.

As gelatin, not only lime-processed gelatin, but also acid-processed gelatin and enzyme-processed gelatin described in *Bull. Soc. Sci. Phot. Japan.*, No. 16, page 30 (1966) may be used. Further, hydrolyzed products or enzymatic products of gelatin can be used, too. As the gelatin derivatives, it is possible to use those prepared by reacting gelatin with various compounds for example, acid halides, acid anhydrides, isocyanates, bromoacetic acid, alkanesultones, vinylsulfonamides, maleinimide compounds, polyalkylene oxides, epoxy compounds, etc. Examples of them have been described in U.S. Pat. Nos. 2,614,928, 3,132,945, 3,186,846 and 3,312,553, British Pat. Nos. 861,414, 1,033,189 and 1,005,784, Japanese Patent Publication No. 26845/67, etc.

As the above described gelatin graft polymers, it is possible to use those obtained by grafting homo- or copolymers of vinyl monomers such as acrylic acid, methacrylic acid, or derivatives thereof such as esters, amides, etc., acrylonitrile, styrene, etc. on gelatin. It is particularly preferred to use graft polymers composed of gelatin and polymers which have a certain degree of compatability with gelatin, such as polymers of acrylic acid, methacrylic acid, acrylamide, methacrylamide, hydroxyalkyl methacrylate, etc. Examples of them have been described in U.S. Pat. Nos. 2,763,625, 2,831,767, 2,956,884, etc.

Examples of typical synthetic hydrophilic high molecular substances include those described in German Patent Application (OLS) No. 2,312,708, U.S. Pat. Nos. 3,620,751 and 3,879,205, and Japanese Patent Publication No. 7561/68.

Further, in the photographic light-sensitive materials of the present invention, it is possible to add dispersions of water insoluble or bed-soluble synthetic polymers to photographic emulsion layers and other hydrophilic colloid layers in order to improve the dimensional stability. For example, it is possible to use polymers composed of one or more monomers selected from alkyl acrylates, alkyl methacrylates, alkoxyalkyl acrylates, alkoxyalkyl methacrylates, glycidyl acrylates, glycidyl methacrylates, acrylamide, methacrylamide, vinyl esters (for example, vinyl acetate), acrylonitrile, olefins, styrene, etc., and polymers composed of a combination of the above described monomers and acrylic acid, methacrylic acid, α,β-unsaturated dicarboxylic acid, hydroxyalkyl acrylate, hydroxyalkyl methacrylate, sulfoalkyl acrylate, sulfoalkyl methacrylate, styrenesulfonic acid, etc. Examples of them include those described in U.S. Pat. Nos. 2,376,005, 2,739,137, 2,853,457, 3,062,674, 3,411,911, 3,488,708, 3,525,620, 3,607,290, 3,635,715, 3,645,740 and British Pat. Nos. 1,186,699 and 1,307,373.

In the light-sensitive materials of the present invention, the hydrophilic colloid layers may be mordanted by cationic polymers in the case that they contain dyes or ultraviolet ray absorbing agents. For example, it is possible to use polymers described in British Pat. No. 685,475, U.S. Pat. Nos. 2,675,316, 2,839,401, 2,882,156, 3,048,487, 3,184,309 and 3,445,231, German Patent Application (OLS) No. 1,914,362 and Japanese Patent Application (OPI) Nos. 47624/75 and 71332/75.

In the photographic light-sensitive materials of the present invention, the photographic emulsion layers and other hydrophilic colloid layers may contain inorganic or organic hardeners. It is possible to use chromium salts (chromium alum, chromium acetate, etc.), aldehydes (formaldehyde, glyoxal, glutaraldehyde, etc.), N-methylol compounds (dimethylolurea, methylol dimethylhydantoin, etc.), dioxane derivatives (2,3-dihydroxydioxane, etc.), active vinyl compounds (1,3,5-triacryloylhexahydro-S-triazine, 1,3-vinylsulfonyl-2-propanol, 1,2-di-(vinylsulfonylacetamido)ethane, etc.), active halogen compounds (2,4-dichloro-6-hydroxy-S-triazine, etc.), and mucohalogenic acids (mucochloric acid, mucophenoxychloric acid, etc.), which are used alone or as a combination thereof.

The photographic emulsion layers and other hydrophilic colloid layers in the light-sensitive materials of the present invention may contain surface active agents for various purposes, for example, as coating assistants, or for prevention of electrically charging, improvement of lubricating property, emulsification, prevention of adhesion, improvement of photographic properties (for example, acceleration of development, hard tone or sensitization), etc.

For example, it is possible to use nonionic surface active agents such as saponin (steroid), alkyleneoxide derivatives (for example, polyethylene glycol, polyethylene glycol/polypropylene glycol condensates, polyethylene glycol alkyl ethers or polyethylene glycol alkylaryl ethers, polyethylene glycol esters, polyethylene glycol sorbitan esters, polyethylene glycol alkylamine or amides, polyethylene oxide adducts of silicone, etc.), glycidol derivatives (for example, alkenylsuccinic acid polyglycerides and alkylphenol polyglycerides), polyhydric alcohol aliphatic acid esters or saccharide alkyl esters, etc.; anionic surface active agents containing acid groups such as a carboxy group, a sulfo group, a phospho group, a sulfate group, a phosphate group, etc., such as alkylcarboxylic acid salts, alkylsulfonic acid salts, alkylbenzenesulfonic acid salts, alkylnaphthalenesulfonic acid salts, alkyl sulfuric acid esters, alkylphosphoric acid esters, N-acyl-N-alkyltaurines, sulfosuccinic acid esters, sulfoalkyl polyoxyethylene alkylphenyl ethers, polyoxyethylene alkylphosphoric acid esters, etc.; ampholytic surface active agents such as amino acids, aminoalkylsulfonic acids, aminoalkylsulfuric acid esters or phosphoric acid esters, alkylbetaines, amine oxides, etc.; and cationic surface active agents such as alkylamine salts, aliphatic or aromatic quaternary ammonium salts, heterocyclic quaternary ammonium salts such as pyridinium salts, imidazolium salts, etc., aliphatic or heterocyclic sulfonium salts, aliphatic or heterocyclic phosphonium salts, etc. In addition, fluorine containing surface active agents may be used.

In the photographic emulsion layers of the photographic light-sensitive materials of the present invention, any of silver bromide, silver iodobromide, silver iodochlorobromide, silver chlorobromide and silver chloride may be used as the silver halide.

The photographic emulsions used in the present invention may be spectrally sensitized by methine dyes or others. Although these sensitizing dyes can be used alone, they may be used as a combination of two or more of them. The combination of the sensitizing dyes is often used for the purpose of supersensitization. The emulsions may contain dyes which do not have a spectral sensitization function themselve or substances which do not substantially absorb visible rays and show supersensization, together with the sensitizing dyes.

Suitable sensitizing dyes, combinations of dyes which show supersensitization and substances which show supersensitization have been described in *Research Disclosure* Vol. 17643 (Dec. 1978) page 23 IV-J.

In the light-sensitive materials of the present invention, the hydrophilic colloid layers may contain water soluble dyes as filter dyes or for the purpose of preventing irradiation or for other purposes. Examples of such dyes include oxonol dyes, hemioxonol dyes, styryl dyes, merocyanine dyes, cyanine dyes and azo dyes. Particularly, oxonol dyes, hemioxonol dyes and merocyanine dyes are useful.

For the purpose of increasing sensitivity, increasing contrast or accelerating development, the photographic emulsion layers of the photographic light-sensitive materials of the present invention may contain, for example, polyalkylene oxide or derivatives thereof such as ethers, esters, amines, etc., thioether compounds, thiomorpholines, quaternary ammonium compounds, urethane derivatives, urea derivatives, imidazole derivatives, 3-pyrazolidones, etc. For example, it is possible to use those described in U.S. Pat. Nos. 2,400,532, 2,423,549, 2,716,062, 3,617,280, 3,772,021 and 3,808,003 British Pat. No. 1,488,991, etc.

In the photographic emulsions used in the present invention, it is possible to incorporate various compounds for the purpose of preventing forgging in the step of production of the light-sensitive materials, during preservation thereof or during photographic processing or for the purpose of stabilizing photographic properties. For example, it is possible to add various known antiffogging agents or stabilizers such as azoles, for example, benzothiazolium salts, nitroimidazoles, triazoles, benzotriazoles or benzimidazoles (particularly, nitro- or halogen substituted benzimidazoles); heterocyclic mercapto compounds, for example, mercaptothiazoles, mercaptobenzothiazoles, mercaptobenzimidazoles, mercaptothiadiazoles, mercaptotetrazoles (particularly, 1-phenyl-5-mercaptotetrazole) or mercaptopyrimidines; the above described heterocyclic mercapto compounds having water soluble groups such as a carboxyl group a sulfo group, etc.; thioketo compounds, for example, oxazolinethione; azaindenes, for example, tetrazaindenes (particularly, 4-hydroxy-(1,3,3a,7)tetrazaindenes); benzenethiosulfonic acids; benzenesulfinic acids, etc.

The light-sensitive materials of the present invention may contain hydroquinone derivatives, aminophenol derivatives, gallic acid derivatives, ascorbic acid derivatives, etc. as anti-color-fogging agents.

In carrying out the present invention, known antifading agents can be used together. Further, the dye image stabilizers used in the present invention can be used alone or as a mixture of two or more thereof. Examples of the known antifading agents include hydroquinone derivatives, gallic acid derivatives, p-alkoxyphenols, p-oxyphenol derivatives, bisphenols, etc.

Examples of hydroquinone derivatives have been described in U.S. Pat. Nos. 2,360,290, 2,418,613, 2,675,314, 2,701,197, 2,704,713, 2,728,659, 2,732,300, 2,735,765, 2,710,801 and 2,816,028, British Pat. No. 1,363,921, etc., those of gallic acid derivatives have been described in U.S. Pat. Nos. 3,457,079, 3,069,262, etc., those of p-alkyoxyphenols have been described in U.S. Pat. Nos. 2,735,765 and 3,698,909 and Japanese Patent Publication Nos. 20977/74 and 6623/77, those of p-oxyphenol derivatives have been described in U.S. Pat. Nos. 3,432,300, 3,573,050, 3,574,627 and 3,764,337 and Japenese Patent Application (OPI) Nos. 35633/77, 147434/77 and 152225/77, and those of bisphenols have been described in U.S. Pat. No. 3,700,455.

In the photographic light-sensitive materials of the present invention, the emulsion layers or adjacent layers thereof may contain ultraviolet ray absorbing agents as described, for example, in U.S. Pat. Nos. 3,250,617, 3,253,921, etc., for the purpose of image stabilization.

The present invention can be utilized for light-sensitive materials having a low silver content in which the amount of silver halide in the emulsions in one half to one hundredth of the conventional light-sensitive materials. In such color sensitive materials having a low silver halide content, sufficient color images can be obtained by an image formation process wherein the amount of dyes formed is increased by utilizing color intensification, which comprises using peroxides, cobalt complex salts or sodium chlorite (for example, German Patent Application (OLS) No. 2,357,694, U.S. Pat. Nos. 3,674,490 and 3,761,265, German Patent Application (OLS) No. 2,044,833, 2,056,359, 2,056,360 and 2,226,770, Japanese Patent Application (OPI) Nos. 9728/73 and 9729/73, etc.).

Color development of the photographic light-sensitive materials of the present invention can be carried out by conventional processes known hitherto. Namely, it is possible to use a negative-positive process which comprises carrying out color development with substituted p-phenylenediamine to form a dye image and a silver image, processing with a bleaching bath to oxidize into a silver salt, and removing the residual silver halide and other silver salts by dissolving with using a fixing bath to leave the dye image, and a color reversal process which comprises forming a negative silver image by developing with a developing agent containing a black-and-white developing agent, carrying out at least one uniform exposure or suitable fogging treatment, and subsequently carrying color development, bleaching and fixation to obtain a dye positive image.

Further, in color X-ray films utilizing the developed silver image and the developed dye image, it is possible to use a process comprising color development and fixation which does not comprises bleaching.

The temperature of these color photographic processings is selected from a range of from 18° C. to 50° C., but it is possible to use the temperature of lower than 18° C. or higher than 50° C.

As the p-phenylenediamine derivatives for developing the photographic light-sensitive materials of the present invention, many compounds known hitherto can be used. A particularly suitable p-phenylenediamine developing agent includes N,N-dialkyl-p-phenylenediamine compounds the alkyl groups and the phenyl group of which may be or not substituted. Among them, examples of particularly suitable compounds include N,N-diethyl-p-phenylenediamine hydrochloride, N-methyl-p-phenylenediamine hydrochloride, N,N-dimethyl-p-phenylenediamine hydrochloride, 2-amino-5-(N-ethyl-N-dodecylamino)toluene, N-ethyl-N-($\beta$-methanesulfonamidoethyl-3-methyl-4-aminoaniline sulfate, N-ethyl-N-$\beta$-hydroxyethylaminoaniline, 4-amino-N-(2-methoxyethyl)-N-ethyl-3-methylaniline-p-toluenesulfonate, N,N-diethyl-3-methyl-4-aminoaniline, N-ethyl-N-($\beta$-hydroxyethyl)-3-methyl-4-aminoaniline, etc.

In addition, compounds described in L. F. A. Mason, *Photographic Processing Chemistry* (published by Focal Press, 1966) pages 226–229 and U.S. Pat. Nos. 2,193,015 and 2,592,364 and Japanese Patent Application (OPI) No. 64933/73 may be used.

The color developing solution may contain pH buffer agents, development restrainers, antifogging agents, etc. If necessary, it may contain softeners, preservatives, organic solvents, development accelerators, dye forming couplers, competing couplers, fogging agents, auxiliary developing agents, thickening agents, polycarboxylic acid chelating agents, antioxidants, etc.

The bleaching processing may be carried out simultaneously with the fixing processing, or these processings may be carried out separatively. As the bleaching agent, compounds of polyvalent metal such as iron (III), cobalt (III), chromium (VI), copper (II), etc., peracids, quinones, nitroso compounds, etc. may be used. For example, it is possible to use ferricyanides, bichromates, organic complex salts of iron (III) or cobalt (III), complex salts of aminopolycarboxylic acids such as ethylenediaminetetraacetic acid, nitrilotriacetic acid, 1,3-diamino-2-propanol-tetraacetic acid, etc., or organic acids such as citric acid, tartaric acid, malic acid, etc.; persulfates, permanganates, nitrosophenol, etc. Among them, potassium ferricyanide, sodium (ethylenediaminetetraacetato) iron (III) and ammonium (ethylenediaminetetraacetato) iron (III) are particularly preferred. The (ethylenediaminetetraacetato)iron (III) complex salts are useful for both the bleaching solution and the one-bath bleach-fix solution.

To the bleaching solution or the bleach-fix solution, it is possible to add various additives including bleaching accelerators described in U.S. Pat. Nos. 3,042,520 and 3,241,966 and Japanese Patent Publication Nos. 8506/70 and 8836/70 and thiol compounds described in Japanese Patent Application (OPI) No. 65732/78.

Examples of the fixing agent include thiosulfates (for example, ammonium thiosulfate, sodium thiosulfate, potassium thiosulfate, etc.), thiocyanides (for example, ammonium thiocyanide, sodium thiocyanide, potassium thiocyanide, etc.) and thioether compounds such as 3,6-dithia-1,8-octanediol. These compounds may be used alone or as a mixture of two or more thereof.

The present invention will be described in more detail in the following examples.

EXAMPLE 1

Coating solution (A) was applied to a cellulose triacetate base provided with a subbing layer so as to result in a silver content of 2.25 g/m$^2$, and a protective layer was applied to the resulted layer to obtain Sample [A].

Coating solution (A):

100 g of the cyan coupler: 1-hydroxy-2-{γ-(2,4-di-t-amylphenoxy)butyl}naphthamide (main coupler) was dissolved in a mixture of 100 cc of dibutyl phthalate and 100 cc of ethyl acetate, and the resulted solution was stirred at a high rate together with 1 kg of a 10% aqueous solution of gelatin. 350 g of the resulted emulsion was mixed with 1 kg of a red-sensitive silver iodobromide emulsion (containing 50 g of silver and 60 g of gelatin, and having an iodine content of 6% by mol), and 50 ml of a 2% aqueous solution of 2-hydroxy-4,6-dichloro-S-triazine Na salt was added as a gelatin hardener to obtain Coating solution (A).

The protective layer was provided by applying a 5% aqueous solution of gelatin so as to have a dry film thickness of 1μ.

In addition to the main coupler in the Coating solution (A), the following couplers were added in an amount of 10% by mol of the main coupler to prepare Coating solutions (B) and (C). Using these coating solution Samples [B] and [C] were produced by the same procedure as in Sample [A].

| Coating solution | Coupler |
|---|---|
| (B) | (1) |
| (C) | (3) |

The above described Samples [A], [B] and [C] were exposed stepwise to white light, followed by carrying out development at 38° C. by the following processing steps.

| | |
|---|---|
| 1. Color development | 3 minutes and 15 seconds |
| 2. Bleaching | 6 minutes and 30 seconds |
| 3. Water wash | 3 minutes and 15 seconds |
| 4. Fixation | 6 minutes and 30 seconds |
| 5. Water wash | 3 minutes and 15 seconds |
| 6. Stabilization | 3 minutes and 15 seconds |

The composition of the processing solutions using in each step was as follows.

| | |
|---|---|
| Color developing solution: | |
| Sodium nitrilotriacetate | 1.0 g |
| Sodium sulfite | 4.0 g |
| Sodium carbonate | 30.0 g |
| Potassium bromide | 1.4 g |
| Hydroxylamine sulfate | 2.4 g |
| 4-(N—Ethyl-N—β-hydroxyethylamino)- | |

-continued

| | |
|---|---|
| 2-methylaniline sulfate | 4.5 g |
| Water to make | 1 liter |
| Bleaching solution: | |
| Ammonium bromide | 160.0 g |
| Aqueous ammonia (28%) | 25.0 ml |
| Sodium (ethylenediaminetetraacetato) iron | 130 g |
| Glacial acetic acid | 14 ml |
| Water to make | 1 liter |
| Fixing solution: | |
| Sodium tetrapolyphosphate | 2.0 g |
| Sodium sulfite | 4.0 g |
| Ammonium thiosulfate (70%) | 175.0 ml |
| Sodium bisulfite | 4.6 g |
| Water to make | 1 liter |
| Stabilizing solution: | |
| Formalin | 8.0 ml |
| Water to make | 1 liter |

The density of the processed samples was measured using red light. The results were as follows.

| Sample | DAR coupler added | Fog | Relative sensitivity | Density of shoulder part in density curve | γ |
|---|---|---|---|---|---|
| [A] | — | 0.06 | 100 | 1.83 | 1.2 |
| [B] | (1) | 0.07 | 400 | 1.98 | 1.9 |
| [C] | (3) | 0.06 | 420 | 1.90 | 2.0 |

It is understood from these results that the increase of sensitivity and the hard toning were excellent for Samples [B] and [C] containing the coupler of the present invention as compared with Comparative sample [A], while virtually no increase of fogging was observed.

EXAMPLE 2

Coating solution (D) was applied to a cellulose triacetate base provided with a subbing layer so as to result in a silver content of 2.25 g/m$^2$, and a protective layer was applied to the resulted layer to obtain Sample [D].

Coating solution (D):

100 g of the magenta coupler: 1-(2,4,6-trichlorophenyl)-3-[3-{2-(2,4-di-t-amylphenoxy)butyramido}-benzamido]-5-oxo-pyrazoline (main coupler) was dissolved in a mixture of 100 cc of dibutyl phthalate and 100 cc of ethyl acetate, and the resulted solution was stirred at a high rate together with 1 kg of a 10% aqueous solution of gelatin. 350 g of the resulted emulsion was mixed with 1 kg of a green-sensitive silver iodobromide emulsion (containing 50 g of silver and 60 g of gelatin and having an iodine content of 6% by mol), and 50 ml of a 2% aqueous solution of 2-hydroxy-4,6-dichloro-S-triazine Na salt was added as a gelatin hardener to obtain Coating solution (D).

The protective layer was provided by applying a 5% aqueous solution of gelatine so as to have a dry film thickness of 1μ.

In addition to the main coupler in the Coating solution (D), the following couplers were added in an amount of 10% by mol of the main coupler to prepare Coating solutions (E) and (F). Using these coating solutions, Samples [E] and [F] were produced by the same procedure as in Sample [D].

| Coating solution | Coupler |
|---|---|
| (E) | (29) |
| (F) | (33) |

These Samples [D], [E] and [F] were developed by the processing described in Example 1.

The density of the processed samples was measured using green light. The results were as follows.

| Sample | DAR Coupler added | Fog | Relative sensitivity | Density of shoulder part in density curve | γ |
|---|---|---|---|---|---|
| [D] | — | 0.06 | 100 | 2.20 | 1.7 |
| [E] | (29) | 0.06 | 160 | 2.35 | 2.8 |
| [F] | (33) | 0.07 | 180 | 2.36 | 3.0 |

It is understood from these results that the increase of sensitivity and the hard toning were excellent for Samples [E] and [F] containing the coupler of the present invention as compared with Comparative sample [D], and virtually no increase of fogging was observed.

EXAMPLE 3

Coating solution (G) was applied to a cellulose triacetate base provided with a subbing layer so as to result in a silver content of 2.25 g/m$^2$, and a protective layer was applied to the resulted layer to obtain Sample [G].

Coating solution (G):

100 g of the yellow coupler: α-(4-methoxybenzoyl)-α-(1-benzyl-5-ethoxy-3-hydantoinyl)-5-dodecyloxycarbonyl-2-chloroacetanilide (main coupler) was dissolved in a mixture of 100 cc of dibutyl phthalate and 100 cc of ethyl acetate, and the resulted solution was stirred at a high rate together with 1 kg of a 10% aqueous solution of gelatin. 350 g of the resulted emulsion was mixed with 1 kg of a blue-sensitive silver iodobromide emulsion (containing 50 g of silver and 60 g gelatin and having an iodine content of 6% by mol), and 50 ml of a 2% aqueous solution of 2-hydroxy-4,6-dichloro-S-triazine Na salt was added as a gelatin hardener to obtain Coating solution (G).

The protective layer was provided by applying a 5% aqueous solution of gelatine so as to have a dry film thickness of 1μ.

In addition to the main coupler in the Coating solution (G), the following couplers were added in an amount of 10% by mol of the main coupler to prepare Coating solutions (H) and (I). Using these coating solutions, Samples [H] and [I] were produced by the same procedure as in Sample [G].

| Coating solution | Coupler |
|---|---|
| (H) | (44) |
| (I) | (50) |

These Samples [G], [H] and [I] were developed by the processing described in Example 1.

The density of the processed samples was measured using blue light. The results were as follows.

| Sample | DAR Coupler added | Fog | Relative sensitivity | Density of shoulder part in density curve | γ |
|---|---|---|---|---|---|
| [G] | — | 0.06 | 100 | 2.03 | 1.6 |
| [H] | (44) | 0.06 | 240 | 2.14 | 2.5 |
| [I] | (50) | 0.06 | 282 | 2.19 | 2.8 |

It is understood from these results that the increase of sensitivity and the hard toning were excellent for Samples [H] and [I] containing the coupler of the present invention as compared with Comparative sample [G] and virtually no increase of fogging was observed.

EXAMPLE 4

Sample [J] was obtained by applying the following layers in turns to a cellulose triacetate base having a subbing layer so as to have the layer construction described in the following.

The first layer (Antihalation layer):

A 6% aqueous solution of gelatin containing black colloidal silver (silver content 50 g/kg) was applied so as to have a dry film thickness of 1μ.

The second layer (Intermediate layer):

100 g of 2,5-di-t-octylhydroquinone was dissolved in a mixture of 100 g of tricresyl phosphate and 200 g of ethyl acetate, and the resulted solution was mixed with 1 kg of a 10% aqueous solution of gelatin containing 1 g of potassium dodecylbenzenesulfonate and stirred compulsorily by a high-speed homogenizer. 100 g of the resulted emulsion was mixed with 1 kg of a 6% aqueous solution of gelatin, and 50 ml of a 2% aqueous solution of 2-hydroxy-4,6-dichloro-S-triazine Na salt was added as a gelatin hardener thereto. The resulting mixture was applied so as to have a dry film thickness of 1μ. The third layer (Red-sensitive emulsion layer):

Coating solution (A) in Example 1 was applied so as to result in a silver content of 20 mg/100 cm$^2$. In this case, 50 ml of a 2% aqueous solution of 2-hydroxy-4,6-dichloro-S-triazine Na salt was added as a gelatine hardener to the emulsion.

The fourth layer (Intermediate layer):

The same layer as the second layer was formed.

The fifth layer (Green-sensitive emulsion layer):

To 11 g of a green-sensitive silver iodobromide emulsion, 300 g of Emulsion (M) having the following composition and 50 ml of an aqueous solution of the gelatin hardener: 2-hydroxy-4,6-dichloro-S-triazine Na salt were added. The resulted mixture was applied so as to result in a silver content of 20 mg/100 cm$^2$.

| Emulsion (M) | |
|---|---|
| (1) 10% aqueous solution of gelatin | 1 kg |
| (2) The following magenta coupler | 60 g |
| Ethyl acetate | 110 ml |
| Tricresyl phosphate | 65 ml |
| Sodium p-dodecylbenzenesulfonate | 5 g |

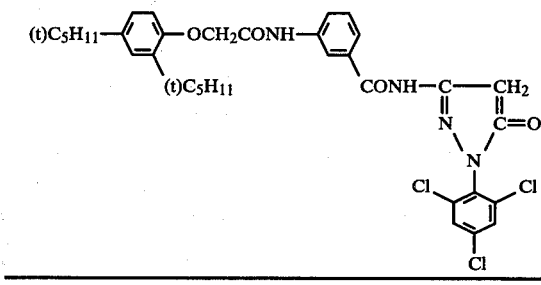

The sixth layer (Yellow filter layer):

To 1 kg of a 6% aqueous solution of gelatin containing 8 g of Carey-Lea yellow colloidal silver, 50 ml of a 2% aqueous solution of 2-hydroxy-4,6-dichloro-S-triazine Na salt was added. The mixture was applied so at to have a dry film thickness of 2μ.

The seventh layer (Blue-sensitive emulsion layer):

To 1 kg of a silver iodobromide emulsion (containing 6.5 g of silver iodobromide (iodine: 7% by mol) and 10 g of gelatin), 800 g of Emulsion (Y) having the following composition and 50 ml of a 2% aqueous solution of 2-hydroxy-4,6-dichloro-S-triazine Na salt were added. The resulted mixture was applied so as to result in a silver content of 10 mg/100 cm².

| Emulsion (Y): | |
| --- | --- |
| (1) 10% aqueous solution of gelatin | 1 kg |
| (2) The following yellow coupler | 100 g |
| Ethyl acetate | 120 ml |
| Sodium p-dodecylbenzenesulfonate | 5 g |
| Tricresyl phosphate | 65 ml |

[Chemical structure of yellow coupler]

The eighth layer (Gelatin protective layer):
To 1 kg of a 6% aqueous solution of gelatin, 50 ml of a 2% aqueous solution of 2-hydroxy-4,6-dichloro-S-triazine Na salt was added. The resulted mixture was applied so as to have a dry film thickness of 1µ.

Using Coating solution (B) in Example 1 instead of Coating solution (A) of the third layer of Sample [J], Sample [K] was produced by applying so as to result in a silver content of 20 mg/100 cm².

These Samples [J] and [K] were developed by the processing described in Example 1.

The density of the red-sensitive emulsion layer of the processed samples was measured using red light.

The results were as follows.

| Sample | DAR coupler added to red-sensitive emulsion layer | Fog | Relative sensitivity |
| --- | --- | --- | --- |
| [J] | — | 0.14 | 100 |
| [K] | (1) | 0.14 | 357 |

It is understood from these results that the increase of sensitivity was excellent for Sample [K] containing the coupler of the present invention as compared with Comparative sample [J], and virtually no increase of fogging was observed. Further, Sample [K] has excellent granularity in a medium and high density parts as compared with Comparative sample [J].

EXAMPLE 5

Sample [L] was prepared by the same process as in Sample [A] with using Coating solution (L) which was prepared by adding 4-(2-formylhydrazino)anilinocarbonyl-methyl thioethanol in an amount of 10% by mol of the main coupler to Coating solution (A) in Example 1.

The Sample [L] and Sample [B] prepared in Example 1 were developed by the processing described in Example 1.

The density of the processed samples was measured using red light. The results were as follows.

| Sample | Coupler and additive | Fog | Density of shoulder part in density curve |
| --- | --- | --- | --- |
| | Main coupler | | |
| [B] | Coupler (1) | 0.07 | 1.98 |
| [L] | Main coupler 4-(2-formylhydrazino)-anilinocarbonylmethyl thioethanol | 1.38 | 1.97 |

It is understood from these results that the degree of fogging was very small in Sample [B] containing the coupler of the present invention as compared with the development accelerator: 4-(2-formylhydrazino)anilinocarboxymethyl thioethanol, and the coupler of the present invention promotes imagewise development.

EXAMPLE 6

After the Samples [A], [B] [C] prepared in Example 1 were exposed stepwise to white light, they were subjected to the following color reversal processing.

| Processing step | Temperature | Time |
| --- | --- | --- |
| The first development | 38° C. | 3 minutes |
| Water wash | " | 1 minute |
| Reversal | " | 2 minutes |
| Color development | " | 6 minutes |
| Conditioning | " | 2 minutes |
| Bleaching | " | 6 minutes |
| Fixation | " | 4 minutes |
| Water wash | " | 4 minutes |
| Stabilization | " | 1 minute |
| Drying | | |

The composition of each processing solution in each processing step is as follows.

| The first development: | |
| --- | --- |
| Water | 800 ml |
| Sodium tetrapolyphosphate | 2.0 g |
| Sodium bisulfite | 8.0 g |
| Sodium sulfite | 37.0 g |
| 1-Phenyl-3-pyrazolidone | 0.35 g |
| Hydroquinone | 5.5 g |
| Sodium carbonate (1 hydrate) | 28.0 g |
| Potassium bromide | 1.5 g |
| Potassium iodide | 13.0 mg |
| Sodium thiocyanide | 1.4 g |
| Water to make | 1.0 l |
| Reversal: | |
| Water | 800 ml |
| Hexasodium nitrilo-N,N,N—trimethylene-phosphonate | 3.0 g |
| Stannous chloride (2 hydrate) | 1.0 g |
| Sodium hydroxide | 8.0 g |
| Glacial acetic acid | 15.0 ml |
| Water to make | 1.0 l |
| Color development: | |
| Water | 800 ml |
| Sodium tetrapolyphosphate | 2.0 g |
| Benzyl alcohol | 5.0 ml |
| Sodium sulfite | 7.5 g |
| Sodium tertiary phosphate (12 hydrate) | 36.0 g |
| Potassium bromide | 1.0 g |
| Potassium iodide | 90.0 mg |
| Sodium hydroxide | 3.0 g |
| Citrazinic acid | 1.5 g |
| 4-Amino-3-methyl-N—ethyl-β-hydroxyethyl-aniline sesquisulfate monohydrate | 11.0 g |
| Ethylenediamine | 3.0 g |
| Water to make | 1.0 l |
| Conditioning: | |

-continued

| | | |
|---|---|---|
| Water | 800 | ml |
| Glacial acetic acid | 5.0 | ml |
| Sodium hydroxide | 3.0 | g |
| Dimethylaminoethaneisothiourea (2 hydrochloride) | 1.0 | g |
| Water to make | 1.0 | l |
| Bleaching: | | |
| Water | 800 | ml |
| Sodium ethylenediaminetetraacetate (2 hydrate) | 2.0 | g |
| Ammonium (ethylenediaminetetraacetato)-iron (III) (2 hydrate) | 120.0 | g |
| Potassium bromide | 100.0 | g |
| Water to make | 1.0 | l |
| Fixation: | | |
| Water | 800 | ml |
| Ammonium thiosulfate | 80.0 | g |
| Sodium sulfite | 5.0 | g |
| Sodium bisulfite | 5.0 | g |
| Water to make | 1.0 | l |
| Stabilization: | | |
| Water | 800 | ml |
| Formalin (37% by weight) | 5.0 | ml |
| Fuji Drywel | 5.0 | ml |
| Water to make | 1.0 | l |

The density of the processed samples was measured using red light. The results were as follows.

| Sample | DAR coupler added | γ | Maximum density |
|---|---|---|---|
| [A] | — | 1.4 | 1.95 |
| [B] | (1) | 2.3 | 2.47 |
| [C] | (3) | 2.5 | 2.46 |

It is understood from these results that the maximum density and the gamma in Samples [B] and [C] containing the couplers of the present invention were higher than those of Comparative sample [A], and the couplers of the present invention showed a very large function of accelerating color development.

EXAMPLE 7

To a blue-dyed polyethylene terephthalate base equipped with a subbing layer, Coating solution (P) was applied so as to result in a silver content of 4.5 g/m², and a protective layer was provided thereon to obtain Sample [P].

Coating solution (P):

100 g of the cyan coupler: 1-hydroxy-4-($\beta$-carboxymethylthioethoxy)-N-n-hexadecyl-2-nathamide (main coupler) was dissolved in a mixture of 100 cc of dibutyl phthalate and 100 cc of ethyl acetate, and the resulting solution was mixed with 1 kg of a 10% aqueous solution of gelatin by stirring at a high rate. 450 g of the resulting emulsion was mixed with 1 kg of a silver iodobromide emulsion (containing 50 g of silver and 60 g of gelatin and having an iodine content of 2% by mol), and 50 ml of a 2% aqueous solution of the gelatin hardener: 2-hydroxy-4,6-dichloro-S-triazine Na salt was added thereto to prepare Coating solution (P).

The protective layer was provided by applying a 5% aqueous solution of gelatin so as to have a dry film thickness of 1 μ.

In addition to the main coupler in Coating solution (P), the following couplers were added in an amount of 5% by mol of the main coupler to prepare Coating solutions (Q) and (R). Using these coating solutions, Samples [Q] and [R] were produced by the same process as in Sample [P].

| Coating solution | Coupler |
|---|---|
| (Q) | (1) |
| (R) | (3) |

After the above described Samples [P], [Q] and [R] were exposed stepwise to white light, they were developed at 35° C. by the following steps.

| | |
|---|---|
| 1. Color development | 25 seconds |
| 2. Fixation | 25 seconds |
| 3. Water wash | 25 seconds |

The composition of the processing solution used in the color development was as follows.

| | |
|---|---|
| Hydroxylamine sulfate | 3.0 g |
| 2-Methylimidazole | 4.0 g |
| 4-(N—Ethyl-N—methoxyethylamino)-2-methyl aniline | 15.0 g |
| Sodium sulfite | 5.0 g |
| Disodium ethylenediaminetetraacetate | 2.0 g |
| Potassium bromide | 0.5 g |
| Potassium carbonate | 50 g |
| 5-Nitroimidazole | 0.1 g |
| Phenidone | 1.5 g |
| Water to make | 1 liter |
| | PH 10.8 |

The fixing bath used was the same as that described in Example 1.

When the optical density of the processed samples was measured, the following results were obtained. The density measured was the total density (developed silver + developed dye).

| Sample | DAR coupler added | Fog | Relative sensitivity | Maximum density |
|---|---|---|---|---|
| [P] | | 0.18 | 100 | 2.41 |
| [Q] | (1) | 0.18 | 214 | 2.85 |
| [R] | (3) | 0.18 | 215 | 2.90 |

It is understood from these results that the increase of sensitivity and the increase of maximum density were excellent in Samples [Q] and [R], containing couplers of the present invention, as compared with the Comparative sample [P], and virtually no increase of fogging was observed. Thus the couplers of the prevent invention are capable of carrying out rapid processing and are suitable for X-ray sensitive materials utilizing dyes.

While the invention has been described in detail and with reference to specific embodiments thereof, it will be apparent to one skilled in the art that various changes and modifications can be made therein without departing from the spirit and scope thereof.

What is claimed is:

1. A silver halide photographic light-sensitive material comprising a layer containing a coupler compound represented by formula (II)

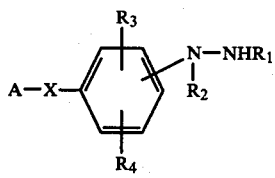 (II)

wherein A represents a residue of a compound capable of undergoing coupling reaction with an oxidation product of an aromatic primary amine developing agent by the removal of one hydrogen atom from the active portion of the said compound; $R_1$ represents a formyl group, an acyl group, a sulfonyl group, an alkoxycarbonyl group, a carbamoyl group, or a sulfamoyl group; $R_2$ represents a hydrogen atom, an acetyl group, an ethoxycarbonyl group, or a methanesulfonyl group; each of $R_3$ and $R_4$ represents a hydrogen atom, a lower alkyl group, a lower alkoxy group, or a halogen atom; and X represents a divalent linking group bonding A to through a hetero atom.

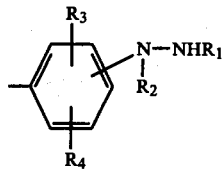

2. A silver halide photographic light-sensitive material as in claim 1, wherein A represents a residue of a cyan coupler, a magenta coupler, a yellow coupler or a noncoloring coupler formed by the removal of one hydrogen atom from the active position of said coupler.

3. A silver halide photographic light-sensitive material as in claim 1, wherein X comprises one or more divalent groups selected from alkylene, phenylene, alkenylene, ether, thioether, amide, thioamide, sulfonamide, ester, sulfon, urea, thiourea, and a heterocyclic ring.

4. A silver halide photographic light-sensitive material as in claim 1, wherein said hetero atom is an oxygen atom, a sulfur atom or a nitrogen atom.

* * * * *